United States Patent
Howard et al.

(10) Patent No.: US 11,028,063 B2
(45) Date of Patent: *Jun. 8, 2021

(54) PROCESSES FOR PRODUCING 2,5-FURANDICARBOXYLIC ACID AND DERIVATIVES THEREOF AND POLYMERS MADE THEREFROM

(71) Applicants: DUPONT INDUSTRIAL BIOSCIENCES USA, LLC, Wilmington, DE (US); ARCHER DANIELS MIDLAND COMPANY, Decatur, IL (US)

(72) Inventors: Stephen J. Howard, Sherman, IL (US); Kristina A. Kreutzer, Wilmington, DE (US); Bhuma Rajagopalan, Wilmington, DE (US); Eric R. Sacia, Wilmington, DE (US); Alexandra Sanborn, Lincoln, IL (US); Brennan Smith, Decatur, IL (US)

(73) Assignees: DUPONT INDUSTRIAL BIOSCIENCES USA, LLC, Wilmington, DE (US); ARCHER-DANIELS-MIDLAND COMPANY, Decatur, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/946,850

(22) Filed: Jul. 9, 2020

(65) Prior Publication Data

US 2020/0339527 A1    Oct. 29, 2020

Related U.S. Application Data

(63) Continuation of application No. 16/695,977, filed on Nov. 26, 2019, now Pat. No. 10,745,369, which is a
(Continued)

(51) Int. Cl.
  *C07D 307/02* (2006.01)
  *C07D 307/68* (2006.01)
  (Continued)

(52) U.S. Cl.
  CPC ......... *C07D 307/68* (2013.01); *B01J 21/066* (2013.01); *B01J 23/10* (2013.01); *B01J 23/6562* (2013.01);
  (Continued)

(58) Field of Classification Search
  CPC ....... C07D 307/68; C08L 77/10; C07B 33/00; C08G 63/181; C08G 69/32; C08G 69/28;
  (Continued)

(56) References Cited

U.S. PATENT DOCUMENTS 2,551,731 A    5/1951    Drewitt et al.
5,959,066 A    9/1999    Charhonneau et al.
(Continued)

FOREIGN PATENT DOCUMENTS

GB    621971    4/1949
JP    2009-1630    1/2009
(Continued)

OTHER PUBLICATIONS

Chatterjee et al, Chemical Conversion Pathways for Carbohydrates, Green Chemistry, 2015, 17,p. 40-71) . (Year: 2015).*
(Continued)

*Primary Examiner* — Taylor V Oh
(74) *Attorney, Agent, or Firm* — Grüneberg and Myers PLLC

(57) ABSTRACT

An integrated process is useful for producing 2,5-furandicarboxylic acid (FDCA) and/or a derivative thereof from a six-carbon sugar-containing feed. The process includes a) dehydrating a feed containing a six-carbon sugar unit, in the presence of a bromine source and of a solvent, to generate
(Continued)

an oxidation feed that contains at least one of 5-hydroxymethylfurfural (HMF) and/or a derivative or derivatives of HMF in the solvent, together with at least one bromine containing species; b) contacting the oxidation feed from step (a) with a metal catalyst and with an oxygen source under oxidation conditions to produce an oxidation product mixture of at least FDCA and/or a derivative thereof, the solvent, and a residual catalyst; c) purifying and separating the mixture obtained in step (b) to obtain FDCA and/or a derivative thereof and the solvent; and d) recycling at least a portion of the solvent obtained in step (c) to step (a).

15 Claims, 5 Drawing Sheets

Related U.S. Application Data continuation of application No. 15/564,590, filed as application No. PCT/US2016/027191 on Apr. 13, 2016, now Pat. No. 10,538,499.

(60) Provisional application No. 62/201,295, filed on Aug. 5, 2015, provisional application No. 62/147,280, filed on Apr. 14, 2015.

(51) Int. Cl.
| | |
|---|---|
| B01J 21/06 | (2006.01) |
| B01J 23/10 | (2006.01) |
| B01J 23/656 | (2006.01) |
| B01J 23/75 | (2006.01) |
| C07B 33/00 | (2006.01) |
| C07B 63/00 | (2006.01) |
| C08G 69/28 | (2006.01) |
| C08G 69/32 | (2006.01) |
| C08L 77/10 | (2006.01) |
| B01J 31/04 | (2006.01) |
| C08G 63/181 | (2006.01) |

(52) U.S. Cl.
CPC .............. *B01J 23/75* (2013.01); *B01J 31/04* (2013.01); *C07B 33/00* (2013.01); *C07B 63/00* (2013.01); *C08G 63/181* (2013.01); *C08G 69/28* (2013.01); *C08G 69/32* (2013.01); *C08L 77/10* (2013.01); *B01J 2231/70* (2013.01); *Y02P 20/10* (2015.11)

(58) Field of Classification Search
CPC . B01J 21/066; B01J 23/75; B01J 23/10; B01J 23/6562; B01J 2231/70; Y02P 20/125
USPC ......................................................... 549/485
See application file for complete search history.

(56) References Cited

U.S. PATENT DOCUMENTS

| | | | |
|---|---|---|---|
| 6,140,422 A | 10/2000 | Khanarian et al. | |
| 7,385,081 B1 | 6/2008 | Gong | |
| 7,956,203 B2 | 6/2011 | Grushin et al. | |
| 7,985,875 B2 | 7/2011 | Hashmi et al. | |
| 8,143,355 B2 | 3/2012 | Matsuda et al. | |
| 8,231,693 B2 | 7/2012 | Gruter | |
| 8,242,292 B2 | 8/2012 | Yutaka et al. | |
| 8,367,851 B2 | 2/2013 | Lilga et al. | |
| 8,420,769 B2 | 4/2013 | Eritate | |
| 8,519,167 B2 | 8/2013 | De Diego et al. | |
| 8,558,018 B2 | 10/2013 | Sanborn | |
| 8,748,479 B2 | 6/2014 | Shaikh et al. | |
| 8,791,278 B2 | 7/2014 | Shaikh et al. | |
| 8,859,788 B2 | 10/2014 | Partin et al. | |
| 9,260,403 B2 | 2/2016 | Yoshikuni et al. | |
| 9,284,290 B2* | 3/2016 | van Haveren | C07D 307/68 |
| 9,617,234 B1* | 4/2017 | Dumesic | C07D 307/68 |
| 10,538,499 B2* | 1/2020 | Howard | C08G 63/181 |
| 2009/0156841 A1 | 6/2009 | Sanborn et al. | |
| 2010/0212218 A1 | 8/2010 | Gruter | |
| 2011/0092720 A1 | 4/2011 | Yutaka et al. | |
| 2011/0282020 A1 | 11/2011 | Sipos | |
| 2012/0202725 A1 | 8/2012 | Grass et al. | |
| 2012/0220507 A1 | 8/2012 | Grass et al. | |
| 2012/0283452 A1 | 11/2012 | Muñoz de Diego et al. | |
| 2014/0107355 A1 | 4/2014 | Dumesic et al. | |
| 2014/0135449 A1 | 5/2014 | Jeol | |
| 2014/0142328 A1 | 5/2014 | Shaikh et al. | |
| 2014/0205786 A1 | 7/2014 | Nederberg et al. | |
| 2014/0295508 A1 | 10/2014 | Yoshikuni et al. | |
| 2014/0315262 A1 | 10/2014 | Sanborn et al. | |
| 2015/0044927 A1 | 2/2015 | Chan et al. | |
| 2015/0183755 A1* | 7/2015 | Subramaniam | B01J 19/10 |
| | | | 549/485 |
| 2015/0299095 A1 | 10/2015 | Stensrud et al. | |
| 2015/0376154 A1* | 12/2015 | Besson | B01J 21/18 |
| | | | 549/485 |
| 2016/0016926 A1 | 1/2016 | Sanborn | |
| 2017/0355658 A1 | 12/2017 | Ma et al. | |
| 2018/0093961 A1 | 4/2018 | Howard et al. | |

FOREIGN PATENT DOCUMENTS

| | | |
|---|---|---|
| WO | 2008/054804 | 5/2008 |
| WO | 2011/023491 | 3/2011 |
| WO | 2011/023590 | 3/2011 |
| WO | 2013/106136 | 7/2013 |
| WO | 2014/012829 | 1/2014 |
| WO | 2014/070415 | 5/2014 |
| WO | 2014/099438 | 6/2014 |
| WO | 2014/158838 | 10/2014 |
| WO | 2015/094970 | 6/2015 |

OTHER PUBLICATIONS

T.P.Hilditch, "Catalytic Processes in Applied Chemistry", D. Van Nostrand, CO. New, York, p. Xiii-XV, 1929. (Year: 1929).*
Chatterjee et al., Chemical conversion pathways for carbohydrates, Green Chemistry, Sep. 2014, 17, p. 40-71 (Year: 2014).
Extended European Search Report dated Oct. 9, 2018 in European Application EP 16 78 0582.
Mitiakoudis et al., "*Synthesis and Characterization of Furanic Polyamides*," Macromolecules 1991, 24, 830-835 XP009157490.
Office Action dated Mar. 4, 2020 in Indonesian Application No. PID201707724, 3 pages.
International Preliminary Report on Patentability and Written Opinion dated Sep. 7, 2016 in International Application No. PCT/US2016/027191, 8 pages.
International Search Report dated Sep. 7, 2016 in International Application No. PCT/US2016/027191, 3 pages.
Office Action dated Oct. 10, 2020 in Chinese Application No. 201680022208.0 with English translation, 14 pages.

* cited by examiner

PROCESSES FOR PRODUCING 2,5-FURANDICARBOXYLIC ACID AND DERIVATIVES THEREOF AND POLYMERS MADE THEREFROM

CROSS-REFERENCE TO RELATED APPLICATIONS

This application is a continuation of U.S. application Ser. No. 16/695,977, filed on Nov. 26, 2019, which is a continuation of U.S. application Ser. No. 15/564,590, filed on Oct. 5, 2017, which is the national stage entry of International Application No. PCT/US2016/027191, filed Apr. 13, 2016, which itself claims priority to U.S. Provisional Patent Application No. 62/201,295, filed Aug. 5, 2015, and U.S. Provisional Patent Application No. 62/147,280, filed Apr. 14, 2015, the content of each of which is incorporated by reference.

TECHNICAL FIELD

The present invention relates to oxidation methods for producing 2,5-furandicarboxylic acid from six carbon sugars as may be obtained from biological sources, and especially to methods which employ a homogeneous catalyst in a solvent.

BACKGROUND ART

The use of natural products as starting materials for the manufacture of various large-scale chemical and fuel products which are presently made from petroleum- or fossil fuel-based starting materials, or for the manufacture of biobased equivalents or analogs thereto, has been an area of increasing importance. For example, a great deal of research has been conducted into the conversion of natural products into fuels, as a cleaner and, certainly, as a more sustainable alternative to fossil-fuel based energy sources.

Agricultural raw materials such as starch, cellulose, sucrose or inulin are inexpensive and renewable starting materials for the manufacture of hexoses, such as glucose and fructose. It has long been appreciated in turn that glucose and other hexoses, in particular fructose, may be converted into other useful materials, such as 5-hydroxymethyl-2-furaldehyde, also known as 5-hydroxymethylfurfural or simply hydroxymethylfurfural (HMF):

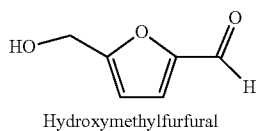

Hydroxymethylfurfural

The sheer abundance of biomass carbohydrates available provides a strong renewable resource base for the development of commodity chemical and fuel products based on HMF. For example, U.S. Pat. No. 7,385,081, issued in June 2008 to Gong, estimates, for example, that of the approximately 200 billion tons of biomass produced annually, 95% was in the form of carbohydrates, and only 3 to 4% of the total carbohydrates were then used for food and other purposes.

In view of this fact, and due to HMF's various functionalities, it has been proposed that the HMF thus obtainable from hexoses such as fructose and glucose, could be utilized to produce a wide range of products derived from renewable resources, such as polymers, solvents, surfactants, pharmaceuticals, and plant protection agents. HMF has in this regard been proposed, as either a starting material or intermediate, in the synthesis of a wide variety of compounds, such as furfuryl dialcohols, dialdehydes, esters, ethers, halides and carboxylic acids.

A number of the products discussed in the literature derive from the oxidation of HMF or of certain derivatives of HMF, especially, ether and ester derivatives of HMF. One such product, 2,5-furandicarboxylic acid (FDCA, also known as dehydromucic acid), has been discussed as a biobased, renewable analog to terephthalic acid in the production of such multi-megaton polyester polymers as polyethylene terephthalate) or poly(butylene terephthalate), as well as a useful monomer for making other commercially valuable polymeric products, for example, in polyamides. FDCA esters have also recently been evaluated as replacements for phthalate plasticizers for PVC, see, e.g., WO 2011/023491A1 and WO 2011/023590A1, both assigned to Evonik Oxeno GmbH, as well as R. D. Sanderson et al., Journal of Appl. Pol. Sci. 1994, vol. 53, pp. 1785-1793.

While FDCA and its derivatives (for example, the ester derivatives just mentioned) have attracted a great deal of recent commercial interest, with FDCA being identified, for instance, by the United States Department of Energy in a 2004 study as one of 12 priority chemicals for establishing the "green" chemical industry of the future, the potential of FDCA (due to its structural similarity to terephthalic acid) to be used in making polyesters, for example, has been recognized at least as early as 1946, see GB 621,971 to Drewitt et al, "Improvements in Polymer".

Unfortunately, viable commercial-scale processes have proven elusive. A threshold challenge has been the development of a commercially viable process to make an HMF or HMF ester or ether derivative from which FDCA could be prepared. Acid-based dehydration methods have long been known for making HMF, being used at least as of 1895 to prepare HMF from levulose (Dull, Chem. Ztg., 19, 216) and from sucrose (Kiermayer, Chem. Zig., 19, 1003). However, these initial syntheses were not practical methods for producing HMF due to low conversion of the starting material to product. Inexpensive inorganic acids such as $H_2SO_4$, $H_3PO_4$, and HCl have been used, but these are used in solution and are difficult to recycle. In order to avoid the regeneration and disposal problems, solid sulfonic acid catalysts have also been used. The solid acid resins have not proven entirely successful as alternatives, however, because of the formation of deactivating humin polymers on the surface of the resins. Still other acid-catalyzed methods for forming HMF from hexose carbohydrates are described in Zhao et al., Science, Jun. 15, 2007, No. 316, pp. 1597-1600 and in Bicker et al., Green Chemistry, 2003, no. 5, pp. 280-284. In Zhao et al., hexoses are treated with a metal salt such as chromium (II) chloride in the presence of an ionic liquid, at 100 degrees Celsius for three hours to result in a 70% yield of HMF, whereas in Bicker et al., sugars are dehydrocyclized to HMF at nearly 70% reported selectivity by the action of sub- or super-critical acetone and a sulfuric acid catalyst.

In the acid-based dehydration methods, additional complications arise from the rehydration of HMF, which yields by-products such as levulinic and formic acids. Another unwanted side reaction includes the polymerization of HMF and/or fructose resulting in humins, which are solid waste products and act as catalyst poisons where solid acid resin catalysts are employed, as just mentioned. Further complications may arise as a result of solvent selection. Water is easy to dispose of and dissolves fructose, but unfortunately, low selectivity and the formation of polymers and humins increases under aqueous conditions.

In consideration of these difficulties and in further consideration of previous efforts toward a commercially viable process for making HMF, Sanborn et al. in US Published Patent Application 2009/0156641A1 (Sanborn et al) describe a method for producing "substantially pure" HMF by heating a carbohydrate starting material (preferably fructose) in a solvent in a column, continuously flowing the heated carbohydrate and solvent through a solid phase catalyst (preferably an acidic ion exchange resin) and using differences in the elution rates of HMF and the other constituents of the product mixture to recover a "substantially pure" HMF product, where "substantially pure" is described as meaning a purity of about 70% or greater, optionally about 80% or greater, or about 90% or greater. An alternative method for producing HMF esters performs the conversion in the presence of an organic acid, which can also serve as the solvent. Acetic acid is mentioned in particular as a solvent for fructose. The resulting acetylated HMF product is reported to be "more stable" than HMF, because upon heating HMF is described as decomposing and producing byproducts "that are not easily isolated or removed," page 4, paragraph 0048.

Further, the acetylated HMF is said to be more easily recovered by distillation or by extraction, though filtration, evaporation and combinations of methods for isolating the HMF esters are also described (page 2, para. 0017). The product, HMF ester which may include some residual HMF can then be mixed in one embodiment with organic acid, cobalt acetate, manganese acetate and sodium bromide and oxidized to FDCA in the presence of oxygen and at elevated temperatures and pressures. In the examples, a Parr reactor is used for performing the oxidation.

Still other derivatives of HMF have been prepared for subsequent oxidation to FDCA or to the ester derivatives of FDCA, as shown, for example, in U.S. Pat. No. 8,558,018 to Sanborn et al., wherein 5-(alkoxymethyl)furfural (AMF), 5-(aryloxymethyl)furfural, 5-(cycloalkoxymethyl)furfural and 5-(alkoxycarbonyl)furfural compounds are described as oxidized in the presence of dissolved oxygen and a Co(II), Mn(II), Ce(III) salt catalyst or mixtures thereof to provide FDCA and various other related materials. The products that can be made will understandably vary dependent on the starting material or mix of starting materials, but can include 2,5-furandicarboxylic acid (FDCA) with the inclusion of bromide. When the reactant is an ether derivative of HMF, the products are surprisingly ester derivatives where either both the ether and aldehyde functional groups have been oxidized, or just the ether function group may be oxidized producing one or both of 5-ester-furan-2-acids (i.e., 5-alkoxycarbonylfurancarboxylic acids) or 5-ester-furan aldehydes, (i.e., alkoxycarbonylfurfurals a. k. a 5-(alkoxycarbonyl)furfural).

In relation to the second part of a process for making FDCA from carbohydrates via HMF or a suitable HMF derivative, for example, an ether or ester derivative as just described, a number of other references have also proposed an oxidation in the presence of very similar catalyst systems to that proposed in Sanborn et al. Thus, for example, in U.S. Pat. No. 7,956,203 to Grushin et al. (E.I. DuPont de Nemours and Company), furan-2,5-dicarboxylic acid (FDCA) is described as made by contacting an alcohol/aldehyde such as HMF with an oxidant in the presence of a metal bromide catalyst to form a dialdehyde, optionally isolating the dialdehyde, then contacting the dialdehyde with an oxidant in the presence of a metal bromide catalyst to form an acid/aldehyde, with optionally isolating the acid/aldehyde, and finally contacting the acid/aldehyde with an oxidant in the presence of a metal bromide catalyst to form the diacid. Grushin contemplates carrying out this process in the presence of a solvent or solvent mixture comprising an aliphatic $C_2$-$C_6$ monocarboxylic acid, which is preferably acetic acid.

The metal bromide catalyst used in Grushin's process comprises a soluble transition metal compound and soluble bromine-containing compound. One metal or a combination of two or more metals may be used, with the transition metal component preferably being cobalt and/or manganese, optionally but preferably further comprising zirconium. Each of the metal components (Co, Mn, Zr) can be provided in any of their known ionic or combined forms, with metal acetate tetrahydrates being mentioned as preferred. The source of bromide "can be any compound that produces bromide ions in the reaction mixture", col. 6, lines 32-33, e.g., hydrogen bromide, hydrobromic acid, sodium bromide, elemental bromine, benzyl bromide, and tetrabromoethane, with sodium and hydrobromic acid being mentioned as preferred.

In U.S. Pat. No. 8,242,292 to Yutaka et al. (Canon Kabushiki Kaisha), a similar method is described for producing FDCA, wherein yield improvements are attributed to the regulation of water content in the oxidation process. HMF is again brought into contact with an oxidant in an organic acid solvent in the presence of bromine and a metal catalyst while removing water produced by the reaction. The metal catalyst preferably contains Co or Mn, but more preferably contains both of Co and Mn, while Br is described as serving as an initiator for the reaction and as advancing the reaction while reducing Co as a main oxidation catalyst through ion discharge. The manner in which bromine is introduced is not addressed by Tutaka et al., but each of the examples employs sodium bromide.

U.S. Pat. No. 8,519,167 to Muñoz de Diego et al. (Furanix Technologies B.V.) describes a method for the preparation of FDCA and/or an alkyl ester of FDCA through contacting a feed comprising a starting material selected from 5-alkoxymethylfurfural, 2,5-di(alkoxymethyl)furan and a mixture thereof, and optionally further containing HMF, with an oxidant in the presence of an oxidation catalyst comprising at least one of cobalt and manganese (and preferably containing both) as well as a source of bromine, preferably a bromide. The bromine source is described essentially as in Grushin, as including any compound that produces bromide ions in the reaction mixture, with hydrobromic acid and/or sodium bromide being preferred. The starting materials are described as prepared from carbohydrates, then through isolation of a feed for contact with the oxidant.

U.S. Pat. No. 8,791,278 to Shaikh et al. (Eastman Chemical Company) describes a process for making FDCA and/or a dry purified FDCA through oxidizing at least one oxidizable compound in an oxidizable raw material stream in the presence of an oxidizing gas stream, solvent stream and at least one catalyst system. The catalyst system is described as preferably comprised of at least one selected from, but not being limited to, cobalt, bromine and manganese compounds which are soluble in the selected oxidation solvent. The bromine component may be added as elemental bromine, in combined form, or as an anion. "Suitable" sources of bromine include hydrobromic acid, sodium bromide, ammonium bromide, potassium bromide, and tetrabromoethane, with hydrobromic acid and sodium bromide again listed as preferred (as in each of Grushin, Yutaka and Shaikh).

Those familiar with the manufacture of terephthalic acid will be very familiar with the use of such solvent-soluble Co/Mn/Br catalyst systems as taught in the several references just summarized. Metal bromide catalysts employing Co and Mn, and in some cases additional metals such as Zr and/or Ce, have been widely commercially used for the liquid-phase oxidation of para-xylene to terephthalic acid. While there has been some limited work done on alternative catalyst systems for converting HMF (and/or an HMF derivative, e.g. an HMF ether or ester derivative) to FDCA, yet because the HMF to FDCA conversion has been evaluated with the overall objective in mind of making a renewable analog to terephthalic acid, it is perhaps not surprising that the catalysts proposed for use in most of the HMF/HMF derivative to FDCA art, as well as the general reaction parameters and process steps described therein, mirror or at least are strongly correlated to the p-xylene oxidation art. There would be distinct and obvious advantages to a manufacturer's developing and implementing an HMF/HMF derivative to FDCA oxidation technology that closely resembles the existing p-xylene to terephthalic acid oxidation technology that has been so widely used, including, but not being limited to, easing the transition for operations personnel accustomed to the p-xylene process, making use of longstanding catalyst supply relationships and facilitating the use of excess terephthalic acid-manufacturing capacity and associated depreciated capital assets.

However, there is a need for a new, more efficient and more cost effective process that converts sugars to furandicarboxylic acid (FDCA) and/or valuable derivatives thereof, for example, diether, diester, ether-acid, ether-ester, ester-acid, ester-aldehyde, ether-aldehyde, ether-acetal, ester-acetal, acetal-acid, alcohol-acid, alcohol-ester, alcohol-acetal, diol, diacetal and aldehyde-acetal derivatives, that can be used as monomers in polymeric syntheses or as intermediates in other syntheses.

SUMMARY OF THE INVENTION

In one aspect of the present invention, there is an integrated process for producing 2,5-furandicarboxylic acid and/or a derivative thereof from a six carbon sugar-containing feed, comprising:

a) dehydrating a feed comprising a six-carbon sugar unit, in the presence of a bromine source and of a solvent, at an elevated temperature and for a time sufficient to generate an oxidation feed comprised of at least one of 5-hydroxymethylfurfural, an ether derivative of 5-hydroxymethylfurfural or an ester derivative of 5-hydroxymethylfurfural in the solvent, together with at least one bromine containing species;

b) contacting the oxidation feed from step (a) with a metal catalyst and with an oxygen source at an elevated temperature for a time sufficient to produce an oxidation product mixture comprising 2,5-furandicarboxylic acid (FDCA) and/or a derivative of 2,5-furandicarboxylic acid, the solvent, and a residual catalyst;

c) purifying and separating the mixture obtained in step (b) to obtain FDCA and/or a derivative of 2,5-furandicarboxylic acid and the solvent; and d) recycling at least a portion of the solvent obtained in step (c) to step (a).

In certain embodiments, an integrated process of the present invention more generally includes regulating the amount of bromine in the oxidation step by adding to or removing bromine from the oxidation feed prior to the oxidation step.

In certain embodiments, the oxidation feed comprises one or more of inorganic bromide and organic bromide.

In certain embodiments, the metal catalyst for the oxidation step comprises one or more transition metals.

In certain embodiments, the metal catalyst comprises either or both of Co and Mn.

In certain embodiments, the metal catalyst comprises Zr in addition to either or both of Co and Mn.

In certain embodiments, the metal catalyst comprises Ce in addition to either or both of Co and Mn.

In certain embodiments, HBr is employed as a source of bromine in the dehydration step.

In certain embodiments, HBr (as hydrobromic acid) is used as an acid catalyst for the dehydration step, and concurrently serves as a bromine source in the dehydration step and for a subsequent Mid-Century-type oxidation.

In certain embodiments, the bromine source in the dehydration step includes at least one bromine-containing material obtained from the oxidation step and recycled back to the dehydration step.

In certain embodiments, the feed to the process comprises one or more of starch, amylase, galactose, cellulose, hemicellulose, inulin, fructan, glucose, fructose, sucrose, maltose, cellobiose, lactose, and sugar oligomers.

In certain embodiments, the feed is fructose syrup, crystalline fructose, high fructose corn syrup, crude fructose, purified fructose or molasses.

In certain embodiments, as for example based on the dehydration of a six-carbon sugar-containing feed in the form of a product, byproduct or process intermediate stream as received from an existing, operating wet or dry grain milling process, the process further comprises concentrating or diluting the oxidation feed by the removal or addition of solvent prior to the oxidation step.

In certain embodiments, the solvent comprises acetic acid or a mixture of acetic acid and water.

In certain embodiments, the process further includes regulating the water content of the feed to the dehydration step and of the oxidation feed generated therefrom.

In certain embodiments, the water content of a six-carbon sugar-containing feed in the form of a product, byproduct or process intermediate stream as received from an existing, operating wet or dry grain milling process is increased by addition of water thereto to improve the yield of furanic species from the six-carbon sugars that will ultimately be oxidized to FDCA and/or a derivative thereof in the subsequent oxidation step, and the water content of the oxidation feed is adjusted to a lower concentration than supplied to the dehydration step.

In certain embodiments, the solvent further comprises a bromine-containing ionic liquid, for example, a 1-alkylpyridinium bromide or 1,3-dialkylimidazolium bromide.

In certain embodiments, the feed is dehydrated in the presence of a $C_1$-$C_5$ alcohol.

In other embodiments of an integrated process according to the present invention, a portion of the product from the dehydration step is used to produce certain derivative co-products from HMF, with optionally oxidizing at least a portion of these derivative co-products front HMF to also produce FDCA or derivatives thereof.

In one such embodiment, an integrated process is provided including dehydrating a feed comprising a six-carbon sugar unit in the presence of a solvent, at an elevated temperature and for a time sufficient to provide a dehydration product including at least one of 5-hydroxymethylfurfural, an ether derivative of 5-hydroxymethylfurfural or an ester derivative of 5-hydroxymethylfurfural in the solvent;

hydrogenating at least a portion of the dehydration product as a whole or of one or more of the 5-hydroxymethylfurfural, ester or ether derivative of 5-hydroxymethylfurfural materials in the dehydration product to form a reduced derivative or derivatives therefrom; oxidizing a portion of the dehydration product not hydrogenated, if any, and including oxidizing at least a portion of the reduced derivatives, by combination with an oxygen source in the presence of a metal catalyst at an elevated temperature and for a time sufficient to produce an oxidation product comprising 2,5-furandicarboxylic acid and/or a derivative thereof, the solvent and a residual catalyst; purifying and separating the mixture obtained from the oxidation step to obtain FDCA and/or a derivative thereof and the solvent; and recycling at least a portion of the solvent to the dehydration step, wherein either or both of the dehydration and hydrogenation steps are carried out in the presence of a bromine source so that a bromine-containing species, a reduced bromine-containing species or both are included in the materials fed to the oxidation step.

In another such co-product embodiment, an integrated process is provided which includes dehydrating a feed comprising a six-carbon sugar unit in the presence of a solvent, at an elevated temperature and for a time sufficient to provide a dehydration product including at least one of 5-hydroxymethylfurfural, an ether derivative of 5-hydroxymethylfurfural or an ester derivative of 5-hydroxymethylfurfural in the solvent; hydrogenating at least a portion of the dehydration product as a whole or of one or more of the 5-hydroxymethylfurfural, ester or ether derivative of 5-hydroxymethylfurfural materials in the dehydration product to form a reduced derivative or derivatives therefrom; etherifying at least a portion of the reduced derivative or derivatives by combination with an alcohol under conditions effective for forming an ether derivative from a reduced derivative of 5-hydroxymethylfurfural; oxidizing a portion of the dehydration product not hydrogenated, if any, and optionally including oxidizing at least a portion of the reduced derivatives from the hydrogenation step, at least some of the ether derivatives from the etherification step or both reduced derivatives from the hydrogenation step and ether derivatives from the etherification step, by combination with an oxygen source in the presence of a metal catalyst at an elevated temperature and for a time sufficient to produce an oxidation product comprising FDCA and/or a derivative thereof, the solvent and a residual catalyst; purifying and separating the oxidation product mixture to obtain FDCA and/or a derivative thereof and the solvent; and recycling at least a portion of the solvent to the dehydration step, wherein any one or more of the dehydration, hydrogenation and etherification steps are carried out in the presence of a bromine source so that at least one of a bromine-containing species, a reduced bromine-containing species and an etherified reduced bromine-containing species is or are included in the materials fed to the oxidation step.

In another aspect, the present invention relates to the preparation of monomeric derivatives of the FDCA produced by an integrated process as summarized above, wherein FDCA is esterified with a $C_1$-$C_{12}$ aliphatic alcohol or a $C_1$-$C_{12}$ aliphatic diol, under conditions effective for carrying out the esterification and optionally in the presence of a suitable esterification catalyst.

In another aspect, the present invention relates to the preparation of a polyester by transesterification of ester derivatives of 2,5-furandicarboxylic acid with a $C_2$-$C_{12}$ aliphatic diol or a polyol and optionally at least one of a polyalkylene ether glycol, a polyfunctional acid or a polyfunctional hydroxyl acid.

In yet another aspect, the present invention relates to preparing a semi-crystalline prepolymer of isoidide with a 2,5-furandicarboxylic acid ester and optionally 1,4-butanediol or 2,3-butanediol by melt polymerization, then performing solid state post condensation on the semi-crystalline prepolymer.

In an aspect, the integrated process further comprises preparing a furan based polyamide compositions comprising contacting an aliphatic or aromatic diamine with 2,5-furandicarboxylic acid and/or derivatives thereof, optionally in the presence of a solvent.

In yet another aspect, the present invention relates to the preparation of a furan based polyamide composition, comprising the steps of dissolving an aromatic diamine monomer in a polar solvent to form a diamine solution under inert atmosphere, wherein the solvent is selected from the group consisting of dimethyl acetamide, dimethyl formamide and dimethyl sulfoxide; adding an aromatic diacid monomer or aromatic diacid derivative component in the form of 2,5-furandicarboxylic acid from the integrated process of the present invention or in the form of a derivative of FDCA from the integrated process to the diamine solution at a temperature in the range of −5 to 35 degrees Celsius to form a reaction mixture; continuing the reaction until there is no further increase in temperature or until a desired viscosity of the reaction mixture is achieved; and isolating the polymer from the reaction mixture.

DESCRIPTION OF EMBODIMENTS OF THE INVENTION

Figure 1:
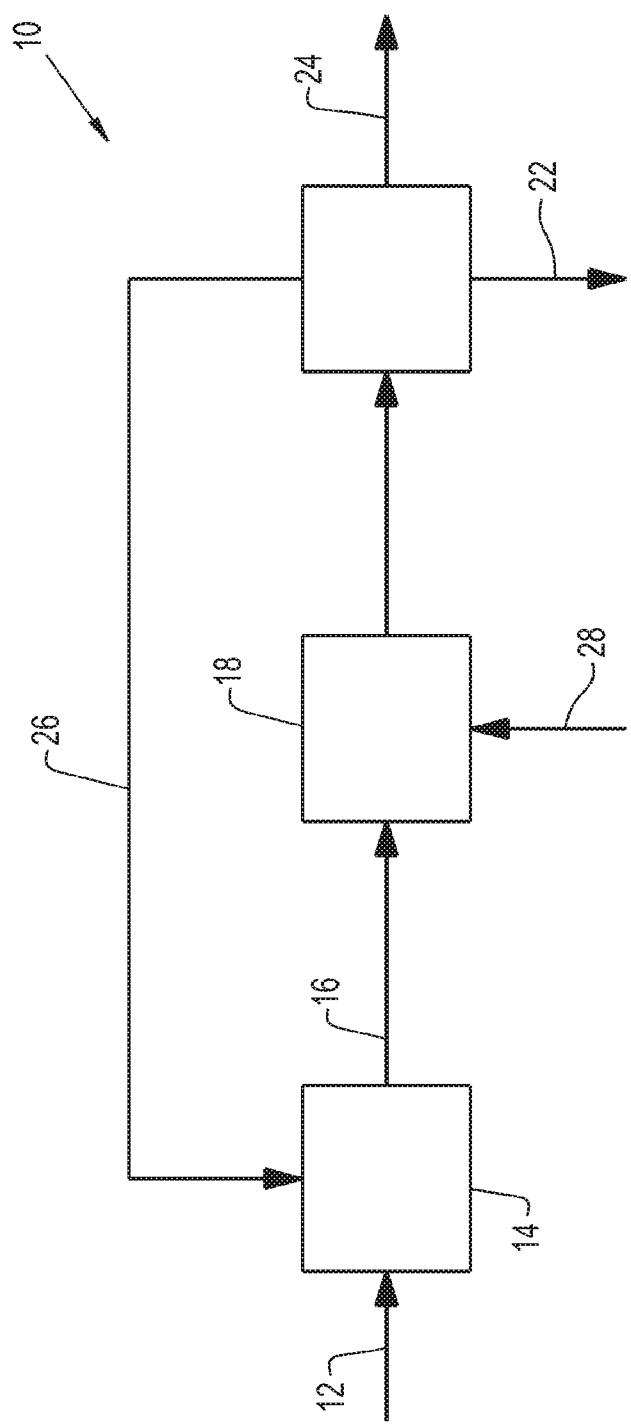
FIG. 1 is a schematic diagram of one illustrative embodiment of an integrated process for making 2,5-furandicarboxylic acid and/or a derivative thereof.

The disclosures of all patent and non-patent literature referenced herein are hereby incorporated in their entireties.

The term "furandicarboxylic acid" is used interchangeably with furan dicarboxylic acid; 2,5-furandicarboxylic acid; 2,4-furan dicarboxylic acid; 3,4-furandicarboxylic acid; and 2,3-furandicarboxylic acid. 2,5-furandicarboxylic acid (FDCA), also known as dehydromucic acid, is an oxidized furan derivative.

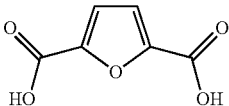 [SMILES: O=C(O)c1ccc(C(=O)O)o1]

| 2,5-Furandicarboxylic acid | |
|---|---|
| IUPAC name | |
| Furan-2,5-dicarboxylic acid | |
| Other names | |
| Dehydromucic acid | |
| Identifiers | |
| CAS number | 3238-40-2 |
| PubChem | 76720 |

A "derivative of 2,5-furandicarboxylic acid" as used above and elsewhere herein shall be understood to include, but not limited to ether, acetal and ester derivatives of 2,5-furandicarboxylic acid and associated 2,5-furandicarboxylic acid precursors, such as 5-hydroxymethylfurfural, 2,5-diformylfuran, and 5-formyl-2-furancarboxylic acid. For example, a "derivative of 2,5-furandicarboxylic acid" may include any derivative combinations thereof, for example, diether, diester, ether-acid, ether-ester, ester-acid, ester-aldehyde, ether-aldehyde, ether-acetal, ester-acetal, acetal-acid, alcohol-acid, alcohol-ester, alcohol-acetal, diol, diacetal and aldehyde-acetal derivatives.

A "six-carbon sugar unit" as used above and elsewhere herein shall be understood as comprising at least one of a six-carbon sugar, an oligomer of a six-carbon sugar, and/or a polymer of a six-carbon sugar.

A "bromine source" as used above and elsewhere herein shall be understood to be any compound that produces bromide ions or radicals in the reaction mixture, e.g., hydrogen bromide, hydrobromic acid, sodium bromide, elemental bromine, benzyl bromide, 5-(bromomethyl)furfural and tetrabromoethane.

A "bromine-containing species" as used above and elsewhere herein shall be understood as comprising one or more of inorganic bromides such as HBr; metal bromides including but not being limited to lithium bromide, sodium bromide, potassium bromide, magnesium bromide, calcium bromide, cobalt bromide and manganese bromide; and organic bromides such as, but not being limited to, 5-(bromomethyl) furfural and derivatives thereof, and brominated furanic oligomers.

A "residual catalyst" as used above and elsewhere herein shall be understood as comprising one or more of bromine-containing species and metal catalyst.

As used in this application, the singular forms "a", "an" and "the" include plural references unless the context clearly indicates otherwise. The term "comprising" and its derivatives, as used herein, are similarly intended to be open ended terms that specify the presence of the stated features, elements, components, groups, integers, and/or steps, but do not exclude the presence of other unstated features, elements, components, groups, integers and/or steps. This understanding also applies to words having similar meanings, such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers, and/or steps. The term "consisting essentially of", as used herein, is intended to specify the presence of the stated features, elements, components, groups, integers, and/or steps, as well as those that do not materially affect the basic and novel characteristic(s) of stated features, elements, components, groups, integers, and/or steps. Terms of degree such as "substantially", "about" and "approximately" as used herein mean a reasonable amount of deviation of the modified term (beyond that degree of deviation understood by the precision (significant figures) with which a quantity is expressed) such that the end result is not significantly changed. These terms of degree should be construed as including a deviation of at least plus or minus five (5) percent from the stated value, provided this deviation would not negate the meaning of the term modified.

The term "biologically-derived" as used herein is used interchangeably with "biobased" or "bioderived", and "biologically-derived", "biobased" and "bioderived" shall all be understood as referring to any chemical compounds, including monomers and polymers, that are obtained, in whole or in any part, from any renewable resources including but not limited to plant, animal, marine materials or forestry materials. The "biobased content" of any such compound shall be understood as the percentage of a compound's carbon content determined to have been Obtained or derived from such renewable resources by ASTM Method D6866. In this regard ASTM Method D6866, similar to radiocarbon dating, compares how much of a decaying carbon isotope remains in a sample to how much would be in the same sample if it were made of entirely recently grown materials. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios first in biobased products compared to petroleum products.

The term "FDCA-forming furanics" as used herein refers to furan ring containing monomeric and dimeric molecules with molecular structure directly presumed to form FDCA throughout the course of oxidation. Examples of FDCA-forming furanics, with acetic acid as solvent, include, but are not limited to, 5-(hydroxymethyl)furfural, 5-(acetoxymethyl)furfural, and 5,5'(oxy-bis(methylene))bis-2-furfural. Examples of non-FDCA forming furanics include, but are not limited to, furfural, 2-(hydroxyacetyl)furan, and 2-(acetoxyacetyl)furan.

The present invention may be more completely understood by describing certain embodiments in greater detail. These embodiments are not to be taken as limiting the scope and breadth of the current invention as more particularly defined in the claims that follow, but are illustrative of the principles behind the invention and demonstrate various ways and options for how those principles can be applied in carrying out the invention.

Thus, unless otherwise indicated, any definitions or embodiments described in this or in other sections are intended to be applicable to all embodiments and aspects of the subjects herein described for which they would be suitable according to the understanding of a person of ordinary skill in the art.

Turning now to FIG. 1, an integrated process 10 of the present invention is schematically depicted in a first illustrative embodiment. A feed 12 comprising a six-carbon sugar unit is dehydrated in a dehydration step 14 in the presence of a bromine source and of a solvent at an elevated temperature and for a time sufficient to generate an oxidation feed 16 comprised of at least one of 5-hydroxymethylfurfural (HMF), an ether derivative of HMF (which is capable of being oxidized to form FDCA or a derivative of FDCA in a Mid-Century type process) or an ester derivative of HMF (which has also been demonstrated as capable of oxidation to form FDCA or a derivative of FDCA in a Mid-Century type process) in the solvent, together with at least one bromine-containing species.

The feed 12 can be any source of a six-carbon sugar unit. In an embodiment, the feed 12 can comprise one or more of starch, amylose, galactose, cellulose, hemicellulose, inulin, fructan, glucose, fructose, sucrose, maltose, cellobiose, lactose, and sugar oligomers. Where the integrated process 10 is implemented in the context of an existing plant wherein such sources of hexose carbohydrates already exist, the feed 12 may be obtained from one or a combination of already existing hexose sources, for example, in the form of a product, byproduct or process intermediate stream as received from an existing, operating wet or dry grain milling process, fructose syrup, crystalline fructose, high fructose corn syrup, crude fructose, purified fructose or molasses.

In certain embodiments, the amount of water in the feed 12 may be adjusted from the water content of a product, byproduct or process intermediate stream as received from an existing, operating wet or dry grain milling process, for example, by combining a plurality of such streams in certain proportions and/or by means of recycling water from the oxidation step 18 via stream 26, to regulate the amount of water entering the process 10 in feed 12.

We have found in this regard that the yield of FDCA-forming furanics from the six-carbon sugars in a feed 12 is increased in the dehydration step 14 by increasing the water content of the feed 12 to a certain point, beyond which, however, the yield of FDCA-forming furanics begins to decline. In the dehydration of an aqueous fructose solution at 150 degrees Celsius with 2 mol percent of HBr added, for example, a water content of from about 8 to about 10 weight percent in a mixture of water and acetic acid (the latter being provided at least in part by recycle in the context of the present invention) appeared to be preferable in terms of the yield of FDCA-forming furanics from dehydrating fructose solutions of varying dry solids concentrations, from 10 weight percent to 20 weight percent to 30 weight percent, with the more dilute fructose solutions also providing higher yields of the FDCA-forming furanics for an acetic acid/water mixture containing this amount of water. As a consequence, it will be preferred in many cases to add a significant amount of water in the dehydration step 14 alongside a product, byproduct or process intermediate stream as received from an existing, operating wet or dry grain milling process.

The bromine source for the dehydration step 14 can be any material that produces bromide ions or radicals in the reaction mixture, e.g., hydrogen bromide, hydrobromic acid, sodium bromide, elemental bromine, benzyl bromide, and tetrabromoethane. In an embodiment, the bromine source for the dehydration step 12 is hydrogen bromide, which could function with the feed 12 as an acid catalyst for the dehydration step 14 in the form of hydrobromic acid.

The solvent for dehydration step 14 preferably comprises acetic acid or a mixture of acetic acid and water, as FDCA and its derivatives are largely insoluble in both of acetic acid and water at oxidation temperatures and as the Mid-Century type oxidations have typically been carried out in acetic acid. In certain other embodiments, in light of U.S. Pat. No. 7,985,875 to Hashmi et al. wherein bromine-containing ionic liquids such as 1-alkylpyridinium bromides and 1,3-dialkylimidazolium bromides are indicated as useful promoters in the presence of acetic acid and water for a Mid-Century-type oxidation of p-xylene to provide terephthalic acid, the solvent for the dehydration step 14 may additionally comprise such a bromine-containing ionic liquid. In another embodiment, the feed 12 is dehydrated in the further presence of an alcohol having at least one carbon.

A variety of methods have been described for carrying out a dehydration of hexoses to provide HMF or derivatives of HMF, typically using acid catalysts, that could be used for accomplishing the dehydration step 14. WO 2013/106136 to Sanborn et al., for example, describes a method for producing HMF or HMF derivatives (e.g., the ester or ether derivatives) from an aqueous hexose sugar solution in which, according to certain embodiments, the acid-catalyzed dehydration step is conducted with rapid heating of the hexose solution from an ambient to a reaction temperature, as well as with rapid cooling of the HMF and/or HMF derivative/unconverted sugar mixture prior to the separation of the fermentation-ready residual sugar product from the HMF and/or HMF derivative product. In addition, the time between when the aqueous hexose solution has been introduced into a reactor and the HMF and/or HMF ether products begin to be cooled is preferably limited.

By accepting limited per-pass conversion to HMF, the overall exposure of the HMF that is funned from any given aqueous hexose solution to acidic, elevated temperature conditions is limited, and preferably little to no unwanted or unusable byproducts such as humins are produced requiring waste treatments. Separation and recovery of the products is simplified and levels of HMF and other hexose dehydration products known to inhibit ethanol production by fermentation are reduced in the residual sugars product to an extent whereby the residual sugars product can be used directly for ethanol fermentation if desired. Processes conducted as described were characterized by very high sugar accountabilities and high conversion efficiencies, with very low losses of sugars being apparent.

US 2009/0156841 by Sanborn et al. provides a method of producing HMF and/or HMF esters from a carbohydrate source by contacting the carbohydrate source with a solid phase acid catalyst. A method of producing HMF esters, in one embodiment, involved heating a carbohydrate starting material with a solvent in a column, and continuously flowing the heated carbohydrate and solvent through a solid phase catalyst in the presence of an organic acid to form a HMF ester. The HMF esters or a mixture of HMF and HMF esters can be oxidized together to provide FDCA in good yields, by combining the HMF ester with an organic acid, cobalt acetate, manganese acetate and sodium bromide in the presence of an oxygen source and at elevated temperatures and pressures.

U.S. Pat. No. 8,558,018 to Sanborn and U.S. Pat. No. 8,519,167 to Muñoz de Diego et al. teach methods whereby HMF ether derivatives formed by carrying out the dehydration in the presence of a $C_1$-$C_5$ alcohol can also be oxidized alone or in mixtures with HMF to yield FDCA and ester derivatives of FDCA, using the same oxidation catalyst systems and substantially the same conditions as used for forming FDCA from HMF, so that in certain embodiments of the integrated process 10, the feed 12 may be dehydrated in the presence of an organic acid or a $C_1$-$C_5$ alcohol to provide an oxidation feed 16 including ester or ether derivatives of HMF or a combination of HMF with ester or ether derivatives of HMF.

Referring back to FIG. 1, the integrated process 10 for producing 2,5-furandicarboxylic acid and/or a derivative thereof from a six carbon sugar-containing feed then broadly comprises contacting an oxidation feed 16 from the dehydration step 14 containing various FDCA-forming, furanics (both newly-generated in the dehydration step 14 and recovered from the oxidation step 18) with a metal catalyst and with an oxygen source 28 at an elevated temperature for a time sufficient to produce an oxidation product mixture comprising 2,5-furandicarboxylic acid (FDCA) and/or a derivative thereof, the solvent, and a residual catalyst. In an embodiment, the oxidation feed 16 can be combined with a source of oxygen 28 before contacting with the metal catalyst.

The oxidation feed 16 comprising at least one bromine containing species provides some or substantially all of the bromine required for the oxidation step 18. Furthermore, the integrated process 10 may further comprise regulating the amount of bromine in the oxidation step 18 by adding to or removing bromine from the oxidation feed 16 prior to the oxidation step 18. Any suitable method can be used to control the amount of bromine in the oxidation feed 16 prior to the oxidation step 18, such as for example using ion exchange to remove additional Br and recycle HBr after ion exchange to the dehydration step 14.

As disclosed herein above, the bromine containing species may comprise one or more of inorganic bromides such as HBr; metal bromides including but not being limited to lithium bromide, sodium bromide, potassium bromide, magnesium bromide, calcium bromide, cobalt bromide and manganese bromide; and organic bromides such as, but not being limited to, 5-(bromomethyl) furfural and derivatives thereof, and brominated furanic oligomers. In an embodiment, a bromine source may be introduced at the oxidation step 18 to supplement the bromine-containing species in the oxidation feed 16 from the dehydration step 14, so that the relative amounts of inorganic and organic bromine in the oxidation feed 16 may be regulated, for example, by means of the nature and amounts of the bromine source(s) in the dehydration step 14 and further bromine source(s) at the oxidation step 18. In certain embodiments, the bromine-containing species in the oxidation feed provide substantially all of the bromine requirements for a Mid-Century type oxidation process carried out according to any conventionally known method and using any of the various so-called metal bromide catalysts described in the art.

Any suitable homogeneous oxidation catalyst can be used which is effective for converting HMF, HMF esters or HMF ethers in the oxidation feed (based on the dehydration method used) to FDCA and/or derivatives of FDCA. The metal catalyst may comprise one or more transition metals. In an embodiment, the metal catalyst comprises either or both of Co and Mn. In another embodiment, the metal catalyst further comprises Zr or Ce. Furthermore, the metal catalyst may react with the bromine present in the bromine containing species and may form insitu metal bromides. In an embodiment, the metal catalyst in the oxidation reaction consists essentially of from 10 to 10000 parts per million or 10 to 8000 parts per million or 59 to 5900 parts per million or 2000 to 4000 parts per million of Co; from 5 to 10000 parts per million or 55 to 5500 parts per million or 200 to 1000 parts per million of Mn; and a bromine source in the oxidation reaction is present in the range of 0.1 to 20000 parts per million or 203 to 20000 parts per million or 10 to 10000 parts per million or 1000 to 2000 parts per million of Br.

The homogeneous oxidation catalyst can be selected from a variety of oxidation catalysts, but is preferably a catalyst based on both cobalt and manganese and suitably containing a source of bromine. Still other metals have previously been found useful for combining with Co/Mn/Br, for example, Zr and/or Ce (see Partenheimer, Catalysis Today, vol. 23, no. 2, pp 69-158 (1995)), and may be included as well. In an embodiment, the metal catalyst consists essentially of Co, Mn, and Br as disclosed hereinabove and Zr from 5 to 10000 parts per million or 50 to 5000 parts per million or 100 to 1000 parts per million. In an embodiment, the metal catalyst consists essentially of Co, Mn, and Br as disclosed hereinabove and Ce from 1 to 10000 parts per million or 10 to 5000 parts per million or 50 to 1000 parts per million.

Each of the metal components can be provided in any of their known ionic forms. Preferably the metal or metals are in a form that is soluble in the reaction solvent. Examples of suitable counterions for cobalt and manganese include, but are not limited to, carbonate, acetate, acetate tetrahydrate and halide, with bromide being the preferred halide. With acetic acid (or a mixture of acetic acid and water) as the solvent, the acetate forms of Co and Mn are conveniently used.

The oxidation step can be performed at a temperature of from 120 to 250 and more particularly 170 to 190 degrees Celsius and at an oxygen partial pressure of from 0.02 to 100 bar or from 0.02 to 21 bar or from 0.2 to 100 bar or 0.2 to 21 bar.

The molar yield of 2,5-furandicarboxylic acid from the oxidation step on the basis of the FDCA-forming furanics in the oxidation feed is at least 60 or 70 or 80 or 90 or 95 percent or any integer percent thereof.

As shown in FIG. 1, the integrated process 10 as disclosed hereinabove also comprises the step 22 of purifying and separating the mixture obtained in the oxidation step 18 to obtain FDCA and/or a derivative thereof 24 and recycling 26 at least a portion of the solvent obtained in the purification step to the dehydration step 14.

Following the oxidation step 18, the FDCA is separated out from the solvent for further purification, and at least a portion of the solvent is recycled via stream 26 as previously mentioned. Since FDCA is largely insoluble in acetic acid or in mixtures of acetic acid and water at mild conditions, separation of the FDCA from the preferred solvent is easily accomplished by filtration or centrifugation.

Purification methods for the FDCA may include those methods described, for example, in U.S. Pat. No. 8,748,479 to Shaikh et al., U.S. Pat. No. 8,791,278 to Shaikh et al. and US 2014/0142328 to Shaikh et al., though any suitable method can be used for purifying the diacid, including, but not limited to crystallization/other methods, prior to conversion of the diacid to other derivatives such as esters and polymers. In U.S. Pat. No. 8,748,479, a crude FDCA product is fed to a crystallization zone, followed by a solid-liquid displacement zone to provide a low impurity slurry stream. The FDCA solids are then dissolved to provide a hydrogenation feed that is then hydrogenated to yield a hydrogenated FDCA composition. This composition is then routed to a second crystallization. A purified wet cake stream containing FDCA is then dried to generate a dry purified FDCA product stream. In U.S. Pat. No. 8,791,278, a secondary oxidation zone is utilized in conjunction with crystallization, and optionally with hydrogenation, to provide a dried, purified FDCA product, whereas in US 2014/0142328, a first low temperature oxidative purification is followed by a high temperature oxidative purification, then by crystallization and drying.

As discussed above, in certain embodiments, a combination of inorganic and organic bromine may desirably be present in the oxidation feed 16. Although not to be bound by any theory, it is believed that the manner and relatedly the form in which the bromine component is introduced into the process of sugar dehydration and subsequent oxidation can lead to overall process synergies. In particular, by introducing a bromine source in the performance of the dehydration step, of another earlier step or a combination generally of such earlier steps (meaning, in advance of the oxidation step) whereby a furanic oxidation precursor or precursors to FDCA or to an FDCA ester product are to be produced for then being oxidized to FDCA or an FDCA ester product, so that an oxidation feed including the furanic oxidation precursor or precursors as well as at least one bromine-containing species is produced, at least equivalent FDCA yields can be achieved with reduced amounts of bromine (as hydrobromic acid) as compared to the circumstance wherein the bromine for the Mid-Century type oxidation is added exclusively at the oxidation step 18 in the form of hydrobromic acid.

The capacity to reduce bromine requirements in the process overall and in the oxidation step in particular can be seen to provide a number of benefits and advantages. Reduced bromine in the higher temperature oxidation step (in the form of hydrogen bromide) can be expected to reduce corrosion in the overall process. Correspondingly, because the bromine is more efficiently used in producing FDCA, improved FDCA yields may in fact be achievable without increasing catalyst requirements and without snaking the conditions of the oxidation reactor more corrosive.

The integrated process as disclosed herein above and below, provides several advantages, including, but not limited to, that use of the same acetic acid or acetic acid and water solvent in the dehydration and oxidation steps enables the use of the more stable AcMF precursor to FDCA, without the need for isolating either HMF or AcMF. Furthermore, the use of common solvent and common bromine source provides an added advantage that the solvent, with or without the bromine source, can be recycled at least in part after the oxidation step into the dehydration step, thereby resulting in significant cost (capex, operating cost, conversion) reduction in taking a feed comprising a six-carbon containing species such as a high fructose syrup (e.g., a high fructose corn syrup) to FDCA. Furthermore, the integrated process of the present invention is amenable for retrofitting to existing oxidation assets and/or existing HFCS assets.

Within the general context of an integrated process having these advantages, however, a complication arises in that while the dehydration step 14 would preferably (as explained above) make use of a feed 12 that is fairly dilute, yet the amount of water implicated in feed 12 and generated in the dehydration step 14 will be greater than ideal for a Mid-Century type oxidation, so that the water content of the oxidation feed will in preferred embodiments need to be limited. Excessive water has in this regard been found to be detrimental to the oxidation step, and limiting the water content in and from the oxidation step will be understood as desirable also for improving FDCA recovery via crystallization, given that FDCA has differing solubilities in mixtures of acetic acid and water with differing amounts of water, see WO 2008/054804 to Lilga et al. At the same time, some water content is beneficial for the oxidation reaction and will be appreciated as helpful for heat management in the oxidation. We would prefer that the water content in the oxidation reactor should be regulated in the range of from about 5 to about 7 percent by weight.

The common bromine source and common solvent aspects of the present invention enable the regulation of the water content in the steps 14 and 18 to the preferred levels in each, as well as the management of the catalyst and solvent in the process and of heat generated in the oxidation step 18, and it will be well within the capabilities of those skilled in the art to determine the design (by composition and volume) of the recycle stream 26 to the dehydration step 14 as well as any additional recycle stream (not shown) to the oxidation step 18 or purges of excess water from the overall process, given the details provided above.

Figure 2:
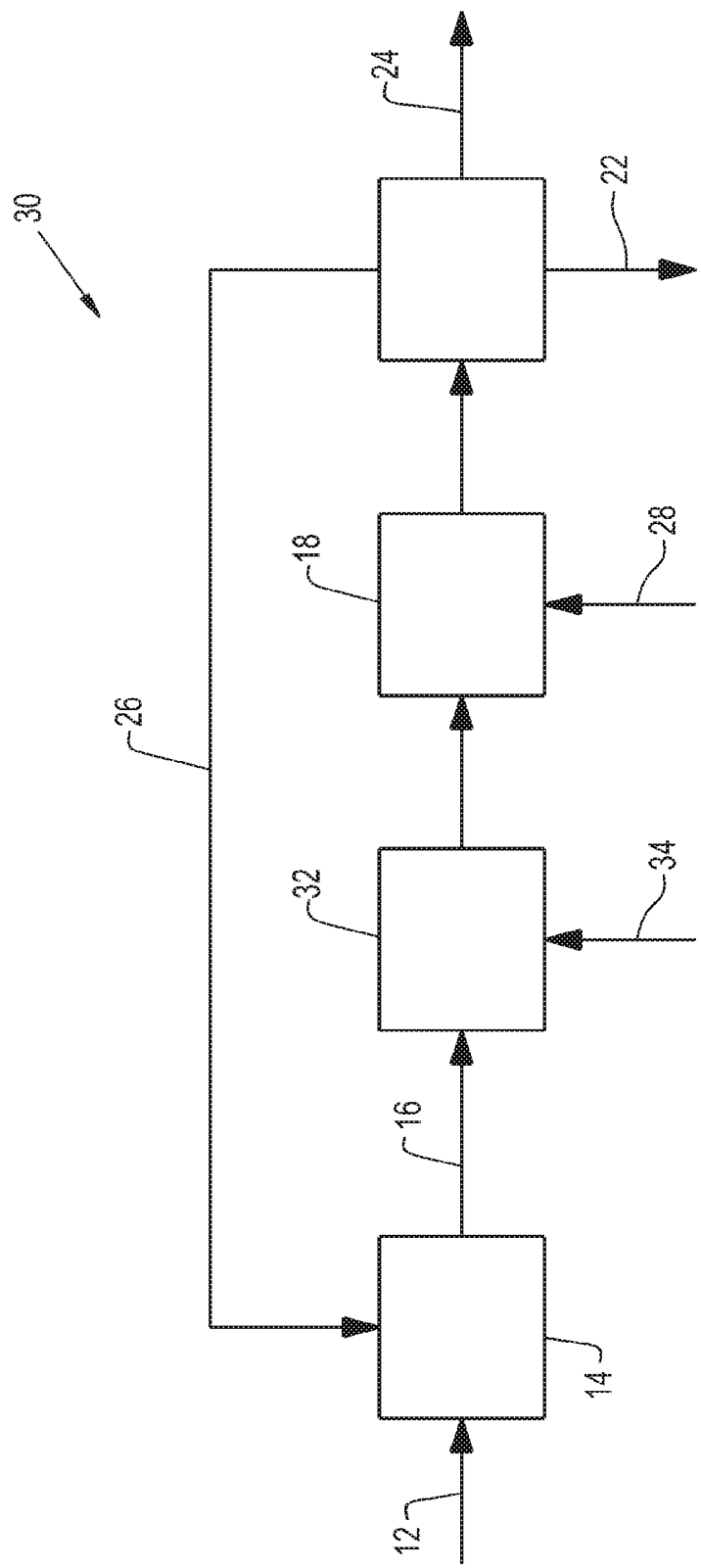
FIG. 2 is a schematic diagram of a second illustrative embodiment of an integrated process for making 2,5-furandicarboxylic and/or a derivative thereof.

FIG. 2 schematically depicts an alternative embodiment 30 of an integrated process according to the present invention, wherein the HMF and/or HMF derivatives produced in the dehydration step 14 are hydrogenated in an hydrogenation step 32 with a source 34 of hydrogen, to provide the reduced derivatives of HMF (furan dimethanol and tetrahydrofuran dimethanol) or of the ester or ether derivatives of HMF and its hydrogenated derivatives. US 2010/0212218 to Gruter, U.S. Pat. No. 8,231,693 to Gruter and U.S. Pat. No. 8,367,851 to Lilga et al, for example, describe methods for forming these reduced derivatives. In US 2010/0212218 and U.S. Pat. No. 8,231,693, the hydrogenation of HMF and HMF ethers, primarily, are respectively described. The reduced derivatives of HMF in US 2010/0212218 are described as stable and independently useful for fine chemical applications, as a pharmaceutical intermediate, in fuels or for oxidation to provide FDCA. U.S. Pat. No. 8,231,693 indicates that the hydrogenation of HMF ether derivatives produces materials useful as fuels and fuel additives, as well as indicating that the reduced HMF ethers may likewise be oxidized to provide FDCA using the same Mid-Century type oxidation methods and catalysts as useful for the conversion of HMF and/or of HMF ethers to FDCA. U.S. Pat. No. 8,367,851 to Lilga et al. for its part relates that furandimethanol and tetrahydrofuran dimethanol also have application in adhesives, sealants, composites, coatings, binders, foams, curatives, polymers, solvents, resins and as monomers.

Figure 3:
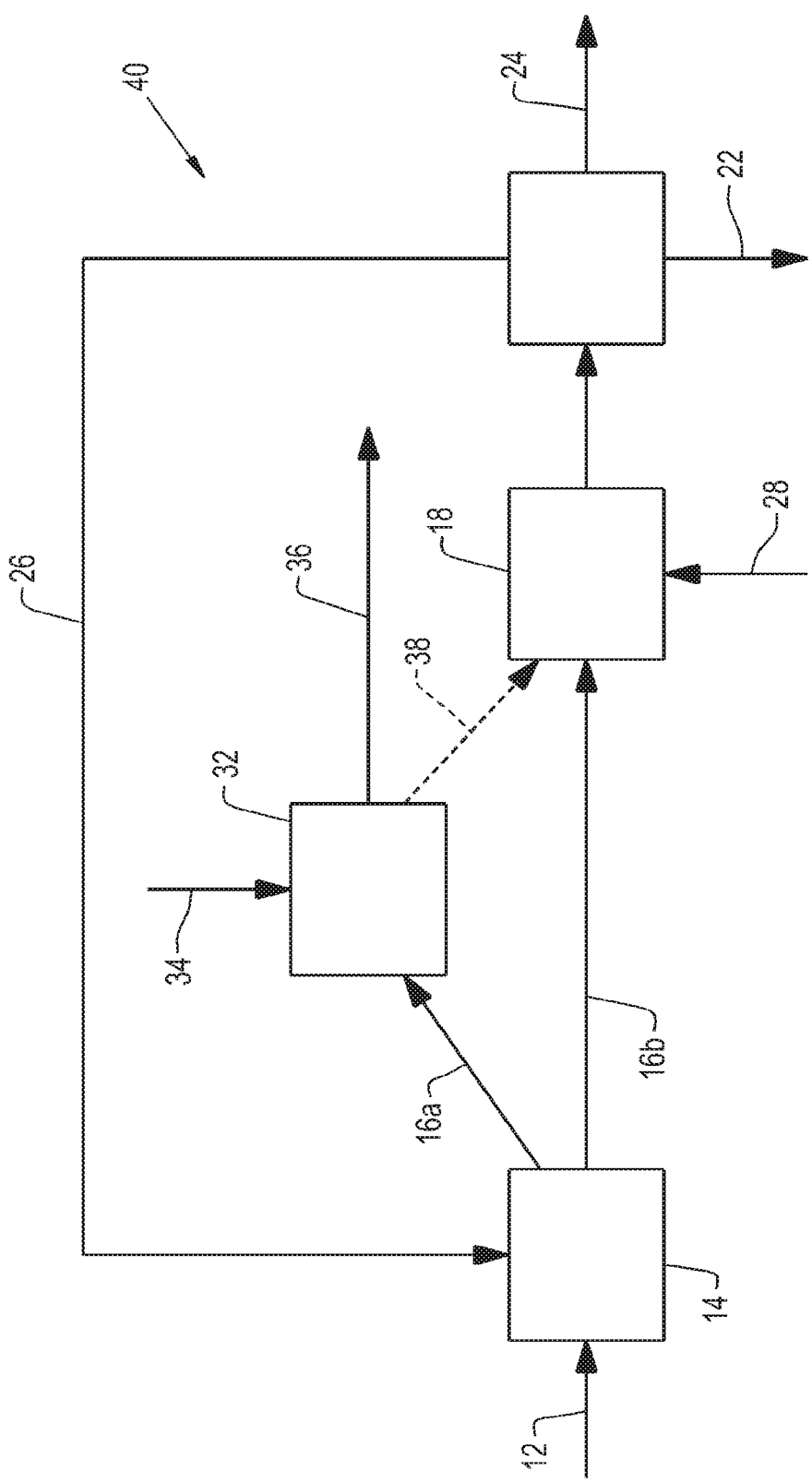
FIG. 3 is a schematic diagram of a third illustrative embodiment of an integrated process for snaking 2,5-furandicarboxylic acid and/or a derivative thereof, together with one or more reduced derivatives of HMF and/or HMF derivatives as co-products.

Because the hydrogenation of HMF and/or of the derivatives of HMF produced in the dehydration step 14 thus provides materials having other possible end uses and applications, in an alternative embodiment 40 shown schematically in FIG. 3, a portion 16a of the HMF and/or HMF derivatives from dehydration step 14 is hydrogenated in hydrogenation step 32 to provide one or more reduced derivatives of HMF and/or of the derivatives of HMF from dehydration step 14 in a product stream 36, while a remaining portion 16b is directly oxidized in oxidation step 18 as in FIG. 1. Optionally, a portion 38 of the reduced derivatives from hydrogenation step 34 may also be oxidized in oxidation step 18 to provide FDCA.

Figure 4:
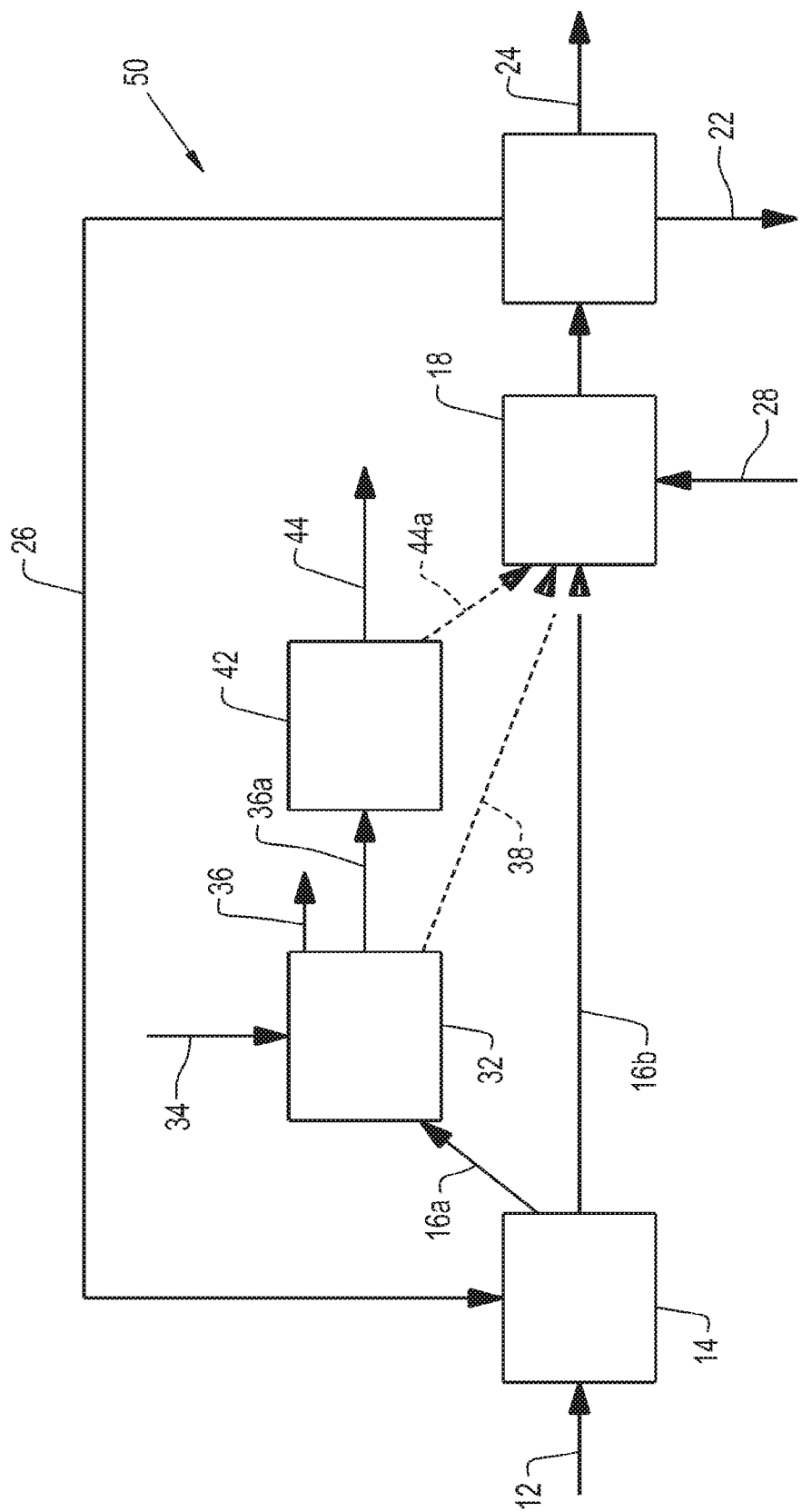
FIG. 4 schematically depicts a fourth illustrative embodiment of an integrated process for making 2,5-furandicarboxylic acid and/or a derivative thereof, together with one or more reduced derivatives and/or one or more etherified reduced derivatives of HMF and/or HMF derivatives as co-products.

FIG. 4 schematically illustrates another co-product scenario 50, wherein an etherification step 42 is performed on a portion 36a of the reduced derivatives of HMF and/or of the derivatives of HMF from dehydration step 14 to produce etherified reduced derivatives of HMF as additional co-products (additional to the reduced products in stream 36) in product stream 44 (though a portion 44a may optionally be oxidized as shown in FIG. 4 in oxidation step 18 to produce FDCA, consistent with U.S. Pat. No. 8,231,693 to Gruter wherein the reduced ether derivatives of HMF are described as suitable for preparing FDCA by oxidation). Thus, in International Patent Application No. PCT/US2014/070021 filed Dec. 12, 2014 for "Mono- and Dialkyl Ethers of Furan-2,5-Dimethanol and (Tetrahydrofuran-2,5-Diyl) Dimethanol and Amphiphilic Derivatives Thereof", and claiming the benefit of U.S. Ser. No. 61/918,239 filed Dec. 19, 2013, a method is described for the etherification of furan dimethanol and tetrahydrofuran dimethanol from the hydrogenation of HMF, and for the preparation of amphiphilic derivatives thereof for use as surfactants and dispersants. More particularly, a process is described for preparing linear mono- and di-alkyl ethers of furan dimethanol and/or of tetrahydrofuran dimethanol which comprises contacting either FDM or THF dimethanol in a polar aprotic organic solvent with a permittivity ($\varepsilon$) >8, at a temperature ranging from −25° C. to 100° C., with either a) an unhindered Brønsted base having a difference in pKa ($\Delta$pKa) ≥15 relative to the pKa of a hydroxyl group of either said FDM or bHMTHF, or b) a hindered Brønsted base and a nucleophile. An alternative method for forming the mono- or dialkyl ethers of FDM and/or THF dimethanol is described in U.S. Provisional Patent Application No. 62/093,730, filed Dec. 18, 2014 for "$CO_2$-Mediated Etherification of Bio-Based Diols", and involves contacting the FDM or THF dimethanol with an alkylating agent in an alcoholic solvent, in the presence of a catalyst that generates in situ a weak acid, at a temperature for a sufficient time to convert the diol to a corresponding alkyl ether. The weak acid is preferably carbonic acid that is formed in situ from hydrated carbon dioxide ($CO_2$) catalyst, and that disappears after depressurization of the reaction. The resulting mono- and dialkyl ethers are indicated as useful biobased replacements for the glycol ethers made commercially from non-renewable resources, as well as for the production of polyethers and epoxides. And, as already mentioned above, U.S. Pat. No. 8,231,693 to Gruter indicates that the etherification and reduction of HMF will produce materials in product stream 44 that would also be useful as fuels or fuel additives.

Figure 5:
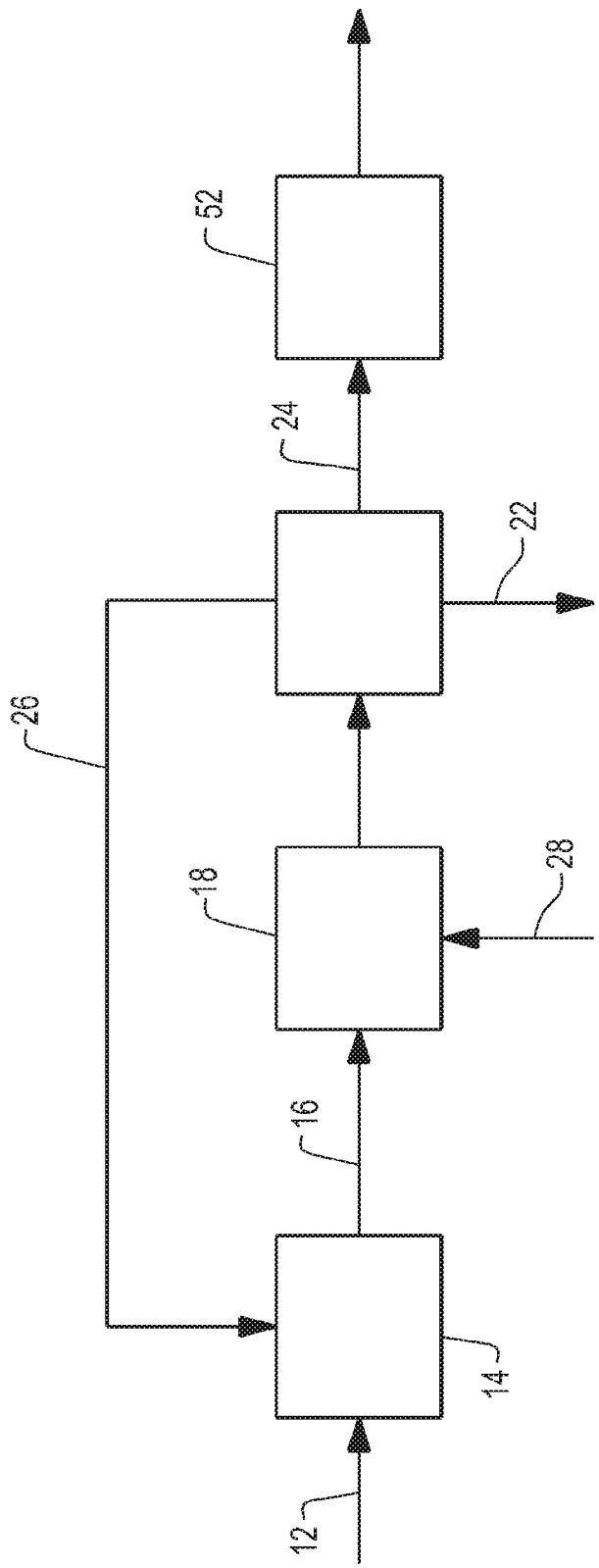
FIG. 5 schematically depicts a process for making further products from the FDCA and/or a derivative of FDCA from an integrated process as shown in FIG. 1, though it will of course be understood that the further products may be equally made from the FDCA produced according to any of the other embodiments schematically shown in FIGS. 2-4.

Turning now to FIG. 5, a process is schematically shown for making further products from the FDCA and/or a derivative of FDCA from an integrated process as shown in FIG. 1, though it will of course be understood that the further products may be equally made from the FDCA produced according to any of the other embodiments schematically shown in FIGS. 2-4.

Thus, in one embodiment of a further process step 52, an esterification can be carried out on the FDCA with a $C_1$-$C_{12}$ aliphatic alcohol or a $C_1$-$C_{12}$ aliphatic diol, under conditions effective for carrying out the esterification and optionally in the presence of a suitable esterification catalyst to prepare monoalkyl and dialkyl furan-2,5-dicarboxylates for subsequent use in polyesters and copolyesters. One such esterification method is described in U.S. Pat. No. 8,859,788 to Partin et al., wherein a purified FDCA solid product in a dried solid form or as a wet cake FDCA composition is fed to an esterification reactor; a liquid reaction mixture is provided in the esterification reactor which comprises FDCA, an alcohol compound, dialkyl furan-2,5-dicarboxylate, water and 5-(alkoxycarbonyl)furan-2-carboxylic acid; an esterification reaction is carried out in the liquid reaction mixture in the presence of the alcohol; passing at least a portion of the vapor in the vapor space, comprising dialkyl furan-2,5-dicarboxylate, unreacted alcohol, 5-(alkoxycarbonyl)furan-2-carboxylic acid and water, into a rectification zone in which at least a portion of the 5-(alkoxycarbonyl)furan-2-carboxylic acid is converted to a liquid phase condensate; contacting at least a portion of the liquid phase condensate with the liquid reaction mixture; and continuously discharging from the rectification zone a dialkyl furan-2,5-dicarboxylate vapor composition comprising dialkyl furan-2,5-dicarboxylate, water, unreacted alcohol and by-products. Another esterification method is described in WO 2014/099438 to Stensrud et al., wherein FDCA is reacted in a liquid reaction system with an alcohol in a $CO_2$-predominant atmosphere without the presence of any other acid catalyst, under conditions corresponding to either supercritical, critical or near-critical temperatures and pressures for the alcohol species and/or $CO_2$ gas. In a variation, the resultant first ester mixture is reacted with a second alcohol in a transesterification reaction to regenerate the first alcohol. WO 2014/070415 to Stensrud et al. relates to still another method, for the alcohol-mediated esterification of FDCA with carbonates, wherein FDCA is reacted with a dialkylcarbonate in the presence of an alcohol-containing solvent and without either an extrinsic acidic or basic catalyst species.

In other embodiments of further processing signified by step 52, the FDCA may be used to prepare a prepolymer or polymer such as a polyester by transesterification of ester derivatives of 2,5-furandicarboxylic acid with a $C_2$ to $C_{12}$ aliphatic diol or a polyol and optionally at least one of a polyalkylene ether glycol (PAEG), a polyfunctional acid or a polyfunctional hydroxyl acid. For example, the FDCA may be used in the manufacture of a polyester as described, for example, in any of US 2014/0205786 to Nederberg et al. (comprising poly(trimethylene furandicarboxylate) from FDCA and 1,3-propanediol); U.S. Pat. No. 6,140,422 to Khanarian et al.; U.S. Pat. No. 5,959,066 to Charbonneau et al.; U.S. Pat. No. 8,420,769 to Eritate; US 2011/0282020 to Sipos; U.S. Pat. No. 8,143,355 to Matsuda et al.; U.S. Pat. No. 2,551,731 to Drewitt et al., "New biobased polyester fiber", Chemical Fibers International January 2014 (describing a polyester made with FDCA and monoethylene glycol (PET)); and JP 2009001630 to Eritate (describing polymers with polyester or polyamide groups whose ester or amide groups are bonded to furan rings and which polyester or polyamide block segments are joined via siloxane groups). The FDCA may also be used to manufacture a polyamide as described, for example, in any of US 2015/0044927 to Chan et at (describing a polymer derived from an aromatic diamine comprising m-phenylene diamine and an aromatic diacid or derivative thereof, especially FDCA or a derivative thereof); WO 2014/012829 to Jeol et al.; US 2014/0135449 to Jeol; and CN 10285054. The integrated process may further comprise the steps of preparing a semi-crystalline prepolymer of isoidide with a 2,5-furandicarboxylic acid ester and optionally 1,4-butanediol or 2,3-butanediol by melt polymerization, then performing solid state post condensation on the semi-crystalline prepolymer.

The integrated process may further comprise preparing a furan based polyamide compositions comprising contacting an aliphatic or aromatic diamine with 2,5-furandicarboxylic acid and/or derivatives thereof, optionally in the presence of a solvent.

The integrated process may further comprise the steps of a) dissolving an aromatic diamine monomer in a polar solvent to form a diamine solution under inert atmosphere, wherein the solvent is selected from the group consisting of dimethyl acetamide, dimethyl formamide and dimethyl sulfoxide, and wherein the aromatic diamine comprises m-phenylene diamine, b) adding an aromatic diacid monomer or aromatic diacid derivative component in the form of 2,5-furandicarboxylic acid from the process of Claim 1 or a derivative thereof to the diamine solution at a temperature in the range of −5 to 35 degrees Celsius to form a reaction mixture; c) continuing the reaction until there is no further increase in temperature or until a desired viscosity of the reaction mixture is achieved; and d) isolating the polymer from the reaction mixture.

The integrated process as disclosed hereinabove can be operated in any suitable configuration/mode such as, batch, continuous and semi batch process.

The present invention is more particularly illustrated by the examples which follow:

EXAMPLES

The methods disclosed herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

All commercial reagents were used as received. ACS grade glacial acetic acid was obtained from Fisher Scientific. All other chemicals were obtained from Sigma-Aldrich (St. Louis, Mo.) unless stated otherwise. Purified 5-(hydroxymethyl)furfural and 5-(acetoxymethyl)furfural as received for use in the oxidation reactions from Archer Daniels Midland Company for certain oxidation feeds (OF-c, OF-d and OF-e in Table 2 below) were synthesized and purified as more particularly described hereafter. 2,5-furan dicarboxylic acid (2,5-FDCA) was obtained from Sarchem Laboratories (Farmingdale, N.J.) in >99% purity. Oxidation intermediates, 2,5-diformylfuran and 5-formyl-2-furancarboxylic acid, were purchased in >98.0% purity from Tokyo Chemical Industry, Co for quantification.

The following abbreviations are or may be used in the examples: "° C." means degrees Celsius; "RPM" means revolutions per minute; "wt %" means weight percent; "g" means gram; "min" means minute(s); "µL" means microliter; "ppm" means microgram per gram, "µm" means micrometer; "mL" means milliliter; "mm" means millimeter and "mL/min" means milliliter per minute; "sccm" means standard cubic centimeters per minute, "DMF" means N,N-Dimethylformamide, "HMF" means 5-(hydroxymethyl)furfural, "AcMF" means 5-(acetoxymethyl)furfural, "DFF" means 2,5-Diformylfuran (known also as 2,5-furandicarbaldehyde), "FFCA" means 5-formyl-2-furancarboxylic acid, "FDCA" means 2,5-furandicarboxylic acid, "OBMF" means 5,5'(oxy-bis(methylene))bis-2-furfural, "Co" means Cobalt, "Mn" means Manganese, "Ti" means Titanium, "Zr" means Zirconium.

General Methods

HPLC Analysis of HMF/AcMF Present in the Oxidation Feed

HPLC analysis was used as one means to quantify yield of oxidation products and conversion of starting materials, and was used to analyze samples containing HMF, AcMF, OBMF, DFF, FFCA, and FDCA before and after reaction. An Agilent 1200 series HPLC equipped with a Zorbax SB-aq column (4.6 mm×250 mm, 5 µm) and photodiode array detector was used for the analysis of the reaction samples. The wavelength used to monitor the reaction was 280 nm.

The HPLC separation of HMF, DFF, FFCA, and FDCA was achieved using an isocratic method with a 1.0 mL/min flow rate of a mobile phase comprising 0.5% v/v trifluoroacetic acid (TFA) in water and a run duration of 30 minutes. The HPLC separation of AcMF and OBMF was achieved using a gradient method with a 1.0 mL/min flow rate combining two mobile phases: Mobile Phase A: 0.5% v/v TFA in water and Mobile Phase B: acetonitrile. In both isocratic and gradient methods, the column was held at 60° C. and 2 µL injections of samples were performed. Analyzed samples were diluted to <0.1 wt % for components of interest in a 50:50 (v/v) acetonitrile/water solvent. The solvent composition and flow rates used for the gradient method is given in Table 1 with linear changes occurring over the corresponding step whenever the composition changes.

TABLE 1

Gradient program for HPLC

| Step | Start time (min) | Volume % Mobile Phase B, at Beginning of Step | Volume % Mobile Phase B, at End of Step |
|---|---|---|---|
| 1 | 0.0 | 0 | 0 |
| 2 | 6.0 | 0 | 80 |
| 3 | 20.0 | 80 | 80 |
| 4 | 25.0 | 80 | 0 |
| 5 | 25.1 | 0 | 0 |
| 6 | 30.0 | 0 | 0 |

Retention times were obtained by injecting analytical standards of each component onto the HPLC. The amount of the analyte in weight percent was typically determined by injection of two or more injections from a given prepared solution and averaging the area measured for the component using the OpenLAB CDS C.01.05 software. The solution analyzed by HPLC was generated by dilution of a measured mass of the oxidation feed solution, oxidation reaction solution, oxidation reaction solids, or oxidation reactor washings with a quantified mass of 50:50 (v/v) acetonitrile/water solvent. Quantification was performed by comparing the areas determined in the OpenLAB software to a linear external calibration curve generated at five or more starting material concentrations. Typical $R^2$ values for the fit of such linear calibration curves was in excess of 0.9997.

While the presented HPLC method was used for this analysis, it should be understood that any HPLC method that can discriminate between FDCA, starting materials, intermediates, impurities, and solvent can be used for this analysis. It should also be understood that while HPLC was used as a method of analysis in this work, other techniques such as gas chromatography could also be optionally used for quantification when employing appropriate derivatization and calibration as necessary.

LAB Color Measurements

A Hunterlab ColorQuest Spectrocolorimeter (Reston, Va.) was used to measure the 2,5-FDCA color. Color numbers are measured as APHA values (Platinum-Cobalt System) according to ASTM D-1209. The "b*" color of 2,5-FDCA is calculated from the UV/VIS spectra and computed by the instrument. Color is commonly expressed in terms of Hunter numbers which correspond to the lightness or darkness ("L") of a sample, the color value ("a*") on a red-green scale, and the color value ("b*") on a yellow-blue scale. In the context of this invention, the "b*" color value is preferably near 0.

Characterization of the Bromine Source in the Bromine Containing Species

The total content of bromine in the oxidation feeds ("Crude Furanics in Acetic Acid"; OF-1 to OF-4) was measured by ICP-MS on a Thermo Element 2 HR-ICP-MS. Ion chromatography measurements were performed using a Dionex ICS-3000 instrument.

The form of the bromine containing species may be characterized by methods such as ICP-MS and Ion Chromatography (IC), Since IC may be used to characterize bromine in an ionic form and ICP-MS provides a measurement of total amount of bromine, it was assumed that the difference between ICP-MS and IC was the amount of covalently bound bromine, which will not be detected in IC. The covalently bound bromine could either be bound to the catalyst metal or bound to organic materials in the oxidation feed.

IC of oxidation feeds was carried out by diluting a sample of an oxidation feed mixture in methylene chloride. Water soluble, ionic bromine was then extracted out using water in a bi-phasic partitioning. A sample of the water phase was then analyzed by IC. This procedure was verified by quantitatively recovering an ionic Br standard by extraction as well. Extraction of the crude oxidation feed liquid was used to minimize precipitation of humins in the water phase and prevent soluble organics from damaging the IC system. IC of oxidation reaction product liquids was carried out by dilution in water and injection for analysis using a Dionex AS17 column.

Examples 1-4: Integrated Production of FDCA in Acetic Acid as Solvent

The integrated process of making FDCA as disclosed herein below comprises the first step (1A) of dehydrating a sugar feed to produce an oxidation feed, with concentrating the crude feed without purification except filtration and followed by the step of oxidation of the as-produced oxidation feed to FDCA.

Step 1A: Production of Crude Oxidation Feed in Acetic Acid (OF-1 to OF-4)

Several oxidation feeds were generated first by combining glacial acetic acid (1182 g, 19.68 mol), aqueous hydrobromic acid solution (at an HBr concentration of 48 wt. % in water; 16.97 g, 0.101 mol), and a mixed fructose/glucose syrup (in a 97/3 ratio by weight of fructose to glucose, 76.88% dry solids basis in water, 1203 g) in a 2 liter Wheaton bottle. These materials were mixed at ambient temperature on a drum roller until homogeneous, then degassed in a sonicator. The concentration of the HBr relative to fructose and glucose was kept constant at 1.99% mol based on HPLC analysis of the feed.

The sugar, acid and water feed solution was then pumped using a 500 cubic centimeter dual piston ISCO pump at a flow rate of 0.55 mL/min into a 66 cm×1.27 cm tubular titanium reactor with a total volume of 62 cubic centimeters. The reactor was packed with solid 3 mm glass beads, and had a void volume of 23 cubic centimeters. The reactor was outfitted with four internal thermocouples and a hot oil jacket for heating and temperature control. The reactor effluent tubing was outfitted with a titanium PTFE/fiberglass diaphragm back pressure regulator and digital pressure sensor to control reactor pressure.

A second 1000 cubic centimeter dual piston ISCO pump was teed into the reactor influent and used to pump pure glacial acetic acid at a flow rate of 1.55 mL/min to produce a total flow rate through the reactor of 2.10 mL/min and a 9.96 min residence time. The final concentration of the total dry solids, fructose, glucose and water in the reactor based on flow rates of the pumps, densities of the solutions and analysis of the HFCS was: 11.2% wt, 10.7% wt, 0.3% wt and 3.4% wt respectively. Flow was established through the reactor and back pressure was applied at 100 psi using the regulator. Once flow was re-established the hot oil temperature was set to 160 C and the reactor was brought to temperature. After the reactor temperature equilibrated, the experiment was run for approximately 5.08 hrs and sampled four times intermittently.

These four samples were prepared and analyzed for furanic components using a Phenomenex PFP analytical column (150 mm×2.1 mm×1.7 um) on a Waters Acquity UPLC equipped with a diode array detector (280 nm) and single quad mass spectrometer (ES+). Residual fructose and glucose were determined through derivatization with pyridine containing O-methylhydroxylamine hydrochloride and acetic anhydride at 80 degrees Celsius, with subsequent analysis using a J&W DB-5 MS UI column (30 m×0.25 mm×0.25 um) on an Agilent 7890 equipped with an HD detector. Water content of the four samples was determined using a Mettler Toledo volumetric Karl Fischer auto-titrator.

The mole yield of furanic oxidation precursors to FDCA—namely, HMF, AcMF and HMF dimer—relative to the total sugar in the feed, and the conversion of fructose and glucose were calculated for each sample, then averaged and measured for standard deviation. Mole yields for the samples ranged from 54.7% to 57.6%, with an average of 56.4% and a standard deviation of 1.2%. Fructose conversions ranged from 97.7% to 98.1%, with an average of 97.9%. The glucose conversions ranged from 44.6% to 46.3%, with an average of 45.2%. Fructose and glucose conversions resulted in a total average conversion of 96.2%, with a standard deviation of 0.20%. No insolubles were observed in any of the samples.

Concentration of the Effluent from the Dehydration Step 1A to Obtain the Oxidation Feed Oxidation feeds generated by dehydration of a 10 wt % sugar feed (97/3 Fructose/glucose), according to procedures outlined in Step 1A, contained 4-5 wt % combined TWIT and AcMF concentrations, as measured by HPLC. Therefore, effluent from the dehydration reactor was concentrated by a factor of approximately 4-6 by rotary evaporation, removing a portion of the acetic acid and water in the mixture. Concentration was performed at a temperature of 25-30° C. and an absolute pressure of 5-15 torr. The resulting mixtures are characterized in Table 2.

Table 2 summarizes the composition of the as-produced oxidation feeds ("Crude Furanics in Acetic Acid") after concentration, including the starting concentrations of FDCA-forming furanics, defined as AcMF, HMF, and OBMF. These components are defined as "FDCA-forming" since they are directly presumed to form FDCA throughout the course of oxidation. Entries OF-1 through OF-4 of Table 2 include "Crude Furanics in Acetic Acid". While the crude oxidation feeds were each filtered through a 2.0 μm HPLC filter prior to oxidation, unless otherwise noted herein, no additional purification was performed to remove unreacted sugars, humins, levulinic acid, or non-FDCA forming furanics (furfural, 2-(hydroxyacetyl)furan, and 2-(acetoxyacetyl) furan).

These oxidation feeds OF-1 through OF-4 were then oxidized under different sets of conditions as described in Step 1B below, to provide Examples 1-4 of the present invention.

TABLE 2

Summary of Major Oxidation Feed Components

| | | FDCA-Forming Furanics in Oxidation Feed [a] | | | Amount and Source of Bromine | | | |
| --- | --- | --- | --- | --- | --- | --- | --- | --- |
| | | | | | | Bromine Added as | | Furanics/Br |
| | | | | | Bromine present from | HBr in | Total | Ratio in |
| Entry | Oxidation Feed (OF) Description: | HMF (wt %) | AcMF (wt %) | OBMF (wt %) | Water (wt %) | Dehydration/Concentration (ppm) | Water (ppm) | Br (ppm) | Feed (mol/mol) |
| OF-1 | Crude Furanics in Acetic Acid - 1 | 5.5 | 13.3 | 0.2 | 1.8[c] | 3800[d] | — | 3800[d] | 26 |
| OF-2 | Crude Furanics in Acetic Acid - 2 | 7.0 | 15.3 | 0.2 | 2.4[c] | 5500[d] | — | 5500[d] | 21 |
| OF-3 | Crude Furanics in Acetic Acid - 3 | 10.4 | 16.8 | 0.3 | 1.7[c] | 5600[d] | — | 5600[d] | 26 |
| OF-4 | Crude Furanics in Acetic Acid - 4 | 9.0 | 18.6 | 0.3 | 1.4[c] | 4900[d] | — | 4900[d] | 30 |
| OF-a | Crude HMF in Water | 46.3 | — | 0.1 | 37[c] | — | — | — | — |
| OF-b | Crude HMF in Water with HBr | 45.4[b] | — | 0.1[b] | 38[b] | — | 9500[b] | 9500[b] | 30 |
| OF-c | Purified Furanics in Acetic Acid | 9.8 | 14.9 | — | <1[b] | — | — | — | — |
| OF-d | Purified Furanics in Acetic Acid with HBr | 9.9 | 15.0 | — | 1.7[b] | — | 5400[b] | 5400[b] | 25 |
| OF-e | Purified Furanics in Acetic Acid with Sugars | 9.9 | 14.8 | — | 20[b] | — | — | — | — |

[a] Measured by HPLC;
[b] Calculated based on quantities of measured materials;
[c] Measured by Karl Fischer Titration;
[d] Measured by ICP-MS Step 1B: Production of FDCA Using the Oxidation Feeds of Step 1A A solution with 140 mL acetic acid, 7.7 mL 1-120 (5 wt % of solution), and dissolved catalyst (cobalt fed as cobalt (II) acetate tetrahydrate, manganese fed as manganese (II) acetate tetrahydrate, HBr (48 wt % concentration in water), and optionally zirconium added as a zirconium acetate solution in acetic acid (Sigma Aldrich, USA—413801)) was added to a 300 mL titanium (Grade 4) Parr autoclave reactor. The amount of catalyst (Co, Mn, Br, or, optionally, Zr) in Table 4 was calculated as below:

$$AmountofCatalyst\ (ppm) = \frac{amountofcatalyst\ (Co, Mn, Br, or Zr)(grams)}{totalamountofsolution\ (grams)} \times 1,000,000$$

wherein the amount of catalyst (grams) includes solely the amount of metal content, Co, Mn, or Zr, and not the mass of the complexes, such as Co(II) acetate; and the amount of bromine and not the entire mass of the bromine source.

The reactor was then assembled and pressurized to ~5.5 bar with air after leak testing. The reactor was then heated to the indicated temperature in Table 4 with 1200 RPM stirring. Once at temperature, the pressure of the reactor was increased to 30 barg with air and a continuous air flow of 600 sccm initiated. Reactor pressure was maintained with a Mity Mite back-pressure regulator on the outlet vapor stream. After the temperature stabilized at the set point, the furanics-containing oxidation feed was introduced at desired rates with the aid of a Scientific Systems, Inc. (SSI) HPLC pump. While the vapor phase was continuously flowing, the liquid phase portion of the reactor was run in a semi-batch configuration wherein the liquid accumulated throughout the course of the run.

After approximately 45 minutes, the tiffanies-containing oxidation feed and air flows were terminated and the reactor was held in batch mode at temperature for an additional 15 minutes. The total mass of liquid feed added throughout the course of the run was recorded. At the end of the batch period, the reactor was quenched with cooling water, depressurized, and disassembled. Typically, an FDCA-containing slurry obtained from the reactor was weighed and filtered. Both the isolated solids and the liquid were analyzed by HPLC. The reactor was then washed with DMF to recover any remaining solids, and the resulting liquid was also analyzed by HPLC. Molar conversion was calculated as the ratio of moles of converted FDCA-forming furanics over the total amount of FDCA-forming furanics fed during the course of a run. Yield of each component was calculated as a ratio of the moles of component produced to the theoretical number of moles of component possible given the oxidation feed's FDCA-forming furanics content.

The results in Table 4 for Examples 1-4 demonstrate a variety of reaction conditions with the feeds described in Table 2. Since the mass of the feed liquid fed throughout the course of a typical semi-batch run in Examples 1-4 ranged from 12.9-13.8 g and the reactor initially contained approximately 156-157 g of acetic acid solution, the bromine in the feed was substantially diluted once in the reactor. It should also be noted here that flow rates below the HPLC pump setpoint of 0.30 mL/min were observed due to the heightened viscosity of the feeds in Examples 1-4. The final bromine concentration in the reactor at the end of a run was approximated using the initial mass, feed mass, and final reactor slurry mass using the following calculation: calculated final Br in reactor (ppm)=(initial reactor solution mass*initial Br concentration (ppm)+feed solution mass*feed solution Br concentration (ppm))/final reaction slurry mass.

Examples 1.1, 1.2, and 1.3 have feeds that span a variety of compositions with respect to both HMF and AcMF and effectively demonstrate the ability of the at least one bromine containing species (see Table 2) present in the oxidation feed to effectively catalyze the oxidation reaction, with conversion in excess of 99% with observable products consisting almost exclusively of FDCA, as shown in Table 4.

Examples 2.1 and 2.2 demonstrate that yields similar to that shown in Example 1 can be maintained due to the presence of at least one bromine containing species in the oxidation feed at elevated temperature and at different Co and Mn loadings.

Examples 3.1-3.3 were performed at an elevated temperature and with additional bromine added in the reactor, which also provided high yields to FDCA when comparing to Examples 2.1 and 2.2.

Examples 4.1 and 4.2 demonstrate that zirconium may also be used as a co-catalyst for oxidation with potentially beneficial results. In this case, addition of 10 mol % Zr with respect to Co was used, providing high yields to FDCA with two separate feed sources.

Characterization of the Bromine Containing Species in Examples 1 and 3

Characterization of Oxidation Feed OF-2 in Table 2 showed a total bromine concentration of 5500 ppm by ICP-MS, of which 2500 ppm was present in an ionic form detectable by IC, therefore implying that the remaining 3000 ppm of the bromine containing species in this oxidation feed were determined to be covalently bound, presumably as 5-(bromomethyl)furfural, brominated humins, and other brominated organics. Results for characterization of feed OF-3 and the reaction liquids after reaction for Examples 1.3 and 3.2 are also shown in Table 3.

TABLE 3

Characterization of Bromine Containing Species in Oxidation Feeds and Post-Reaction Acetic Acid Solution

| | Sample | Total Bromine Measured by ICP-MS (ppm) | Ionic Bromine Measured by IC (ppm) | Covalently Bound Bromine Determined by Difference (ppm) |
|---|---|---|---|---|
| Oxidation Feed before Oxidation Step | OF-2 | 5500 | 2500 | 3000 |
| | OF-3 | 5600 | 2400 | 3200 |
| Sample from Reactor after Oxidation Step | Ex. 1.3 | 520 | 390 | 130 |
| | Ex. 3.2 | 1230 | 850 | 380 |

TABLE 4

Oxidation Reactions with Crude and Purified Oxidation Feeds
Oxidation Reaction Conditions: Oxidation feed rate - 0.12-0.3 mL/min, pressure - 30 barg, oxidant - air, oxidant flow rate: 600 sccm, agitation - 1200 RPM, initial water concentration - 5 wt %, initial catalyst concentration: shown, initial acetic acid amount - 140 mL, liquid feed duration - 45 min, batch post-oxidation duration - 15 min.

| Ex. | Oxidation Feed | Feed Rate (mL/min) | FDCA-forming Furanics Fed (mmol) | Temp (° C.) | Initial Catalyst in Reactor Co (ppm) | Initial Catalyst in Reactor Mn (ppm) |
|---|---|---|---|---|---|---|
| 1.1[a] | OF-1 | 0.3 | 16 | 170 | 2000 | 100 |
| 1.2 | OF-2 | 0.3 | 18.6 | 170 | 2000 | 100 |
| 1.3[a] | OF-3 | 0.3 | 24.7 (1.7) | 170 | 2000 | 100 |
| 2.1 | OF-2 | 0.3 | 19.6 | 200 | 2200 | 130 |
| 2.2 | OF-3 | 0.3 | 24.6 | 200 | 2200 | 130 |
| 3.1 | OF-2 | 0.3 | 20.2 | 200 | 2200 | 130 |
| 3.2[a] | OF-3 | 0.3 | 24.1 (0.3) | 200 | 2200 | 130 |
| 3.3 | OF-4 | 0.3 | 24.6 | 200 | 2200 | 130 |
| 4.1 | OF-2 | 0.3 | 20.2 | 200 | 2200 | 130 |
| 4.2 | OF-3 | 0.3 | 24.3 | 200 | 2200 | 130 |
| Comparative Example A | | | | | | |
| A.1[a] | OF-a | 0.3 | 56.1 (<0.1) | 170 | 2000 | 100 |
| A.2[a] | OF-a | 0.12 | 22.3 (0.2) | 170 | 2000 | 100 |
| A.3[a] | OF-b | 0.12 | 23.2 (0.3) | 170 | 2000 | 100 |
| A.4[b] | OF-a | 0.3 | 54.1 (1.7) | 200 | 2200 | 130 |
| Comparative Example B | | | | | | |
| B.1[a] | OF-d | 0.3 | 25.8 (0.6) | 170 | 2000 | 100 |
| B.2[a] | OF-c | 0.3 | 24.7 (<0.1) | 200 | 2200 | 130 |
| B.3[a] | OF-e | 0.3 | 25.2 (0.4) | 200 | 2200 | 130 |

| Ex. | Initial Catalyst in Reactor Br (ppm) | Initial Catalyst in Reactor Zr (ppm) | Calculated Final Bromine in Reactor Br (ppm) | Conversion/Product Yield Conversion (%) |
|---|---|---|---|---|
| 1.1[a] | 0 | 0 | ~350 | 99 (1) |
| 1.2 | 0 | 0 | 430 | 99.7 |
| 1.3[a] | 0 | 0 | 470 (10) | 99.9 (0.1) |
| 2.1 | 0 | 0 | 470 | 99.8 |
| 2.2 | 0 | 0 | 470 | 99.7 |
| 3.1 | 890 | 0 | 1320 | 99.6 |
| 3.2[a] | 890 | 0 | 1310 (20) | 99.6 (0.2) |
| 3.3 | 890 | 0 | 1270 | 99.8 |
| 4.1 | 890 | 340 | 1330 | 99.5 |
| 4.2 | 890 | 340 | 1320 | 99.4 |
| Comparative Example A | | | | |
| A.1[a] | 370 | 0 | 360 (<10) | 99.7 (<0.1) |
| A.2[a] | 370 | 0 | 370 (<10) | 99.6 (0.3) |
| A.3[a] | 0 | 0 | 390 (<10) | 99.7 (0.3) |
| A.4[b] | 890 | 0 | 850 (<10) | 99.7 (0.1) |

TABLE 4-continued

Oxidation Reactions with Crude and Purified Oxidation Feeds
Oxidation Reaction Conditions: Oxidation feed rate - 0.12-0.3 mL/min,
pressure - 30 barg, oxidant - air, oxidant flow rate: 600 sccm,
agitation - 1200 RPM, initial water concentration - 5 wt %,
initial catalyst concentration: shown, initial acetic acid amount - 140 mL,
liquid feed duration - 45 min, batch post-oxidation duration - 15 min.

| | | Comparative Example B | | |
|---|---|---|---|---|
| B.1[a] | 0 | 0 | 500 (10) | >99.9 |
| B.2[a] | 890 | 0 | 860 (<10) | 99.8 (0.2) |
| B.3[a] | 890 | 0 | 850 (<10) | 99.4 (0.1) |

| | Conversion/Product Yield | | |
|---|---|---|---|
| Ex. | DFF Yield (%) | FFCA Yield (%) | FDCA Yield (%) |
| 1.1[a] | <0.1 | 2 (1) | 83 (3) |
| 1.2 | 0.2 | 2 | 94 |
| 1.3[3] | <0.1 | 1 (1) | 87 (3) |
| 2.1 | 0.3 | 2 | 92 |
| 2.2 | 0.2 | 1 | 86 |
| 3.1 | 0.6 | 4 | 91 |
| 3.2[a] | <0.1 | 1 (<1) | 92 (<1) |
| 3.3 | <0.1 | 1 | 91 |
| 4.1 | 0.1 | 1 | 95 |
| 4.2 | 0.2 | 1 | 89 |
| | Comparative Example A | | |
| A.1[a] | 9 (3) | 18 (1) | 54 (6) |
| A.2[a] | <0.1 | 1 (<1) | 81 (4) |
| A.3[a] | <0.1 | 1 (1) | 76 (5) |
| A.4[b] | 0.9 (0.2) | 3 (<1) | 82 (5) |
| | Comparative Example B | | |
| B.1[a] | <0.1 | 0.2 (0.1) | 68 (3) |
| B.2[a] | <0.1 | 0.5 (0.1) | 72 (<1) |
| B.3[a] | <0.1 | 0.3 (<0.1) | 72 (1) |

Table Notes:
[a]Given value for these runs is average of two runs with standard deviations shown in parentheses.;
[b]Given value for these runs is average of three runs with standard deviations shown in parentheses.

Comparative Example A: Production of FDCA Using Aqueous-Based HMF Feedstock

Step AA: Production of Crude Oxidation Feed in Water (OF-a & OF-b)

For comparison, oxidation feeds OF-a and OF-b were generated in the absence of a bromine source during the dehydration, by direct steam injection heating in a stainless steel tubular reactor of a 15% dry solids solution of 90 percent fructose in water with 0.5 weight percent of sulfuric acid as the catalyst, consistent with Examples 27-32 of US 2014/0315262 to Sanborn et al. More particularly, the mixture was steam injected with 350 psi steam and under a 175 psi system back pressure to a control temperature of 185 degrees Celsius. The residence time was 4 minutes, and produced a dehydration product mixture with 11% final dry solids. The dehydration product mixture was then twice filtered to remove insoluble solids, and purified by adsorbing the HMF onto a Hypersol-Macronet® MN270 divinylbenzene-crosslinked macroporous polystyrene resin (Purolite Corporation, Bala Cynwyd, Pa.) with subsequent desorption with acetone. After stripping off the acetone by pot distilling under vacuum at about 50 degrees Celsius, a material was produced containing about 45 to 50 percent HMF, less than 0.5 percent of acetone and less than 1 percent residual sugars. This material was used as is for oxidation feed OF-a, while oxidation feed OF-b was generated by adding in 9500 parts per million of bromine in the form of a 48 wt. % solution of HBr in water.

Crude "HMF" feeds (OF-a and OF-b) contained crudely purified products of sugar dehydration in a predominantly water solvent without any significant amounts of residual acid. These feeds also contained some small amount of humins, residual sugars, levulinic acid, and non-MCA forming furanics. The oxidation feed OF-b, "Crude HMF in water with HBr," was generated by addition of 48 wt % HBr in water to a feed containing "Crude HMF" (OF-a) to generate a mixture with 9500 ppm Br. While the concentration of Br was higher in this comparative oxidation feed than in the exemplary oxidation feeds (OF-1 to OF-4), the HMF concentration was also equivalently higher; therefore, the furanics:Br ratio in the oxidation feed (defined as the moles of FDCA-forming furanics divided by the moles of Br) was consistent with entries OF-1-4 of Table 2. In cases where Br was added as HBr, the quantity of Br in the oxidation feed was quantified by the amount of the HBr added.

Step AB: Production of FDCA Using the Oxidation Feed of Step AA

A procedure similar to that described in step 1B was used except that the oxidation feeds of Step AA were used. Several reactions with crude HMF feeds in water with bromine (OF-b) or without bromine (OF-a) are summarized with process conditions in Table 4.

Example A.1 and A.2 include an approximately equivalent level of bromine initially in the reactor to that which would be encountered during Example 1 and 2. Example A.1 in Table 4 shows that substantially diminished yields of FDCA are observed at equivalent volumetric flow rates compared to Example 1.3.

Examples A.2 and A.3 in Table 4 are run at lower volumetric flow rates to better match the equivalent molar flow rates of FDCA-forming furanics in Example 1 (see column for "FDCA-forming Furanics Fed"). In Example A.2, bromine is initially in the reactor and the lower feed rate leads to a higher FDCA yield than Example A.1 and a diminished amount of reaction intermediates (DFF and FFCA). However, FDCA yields are still lower than Example 1.3. In Example A.3, HBr is mixed with the oxidation feed (OF-b) to provide a final reactor bromine concentration of 390 ppm in a Br introduction scheme similar to Examples 1 and 2, but the FDCA yields are substantially lower.

Finally, Example A.4 provides a comparison to Example 3.2 at comparable volumetric flow rates and demonstrates that the yield to FDCA is higher using an integrated processing scheme wherein the oxidation is performed using the reactor effluent from sugar dehydration in acetic acid with HBr.

Comparative Example B: Production of FDCA in Acetic Acid as Solvent Using Purified Oxidation Feed with HBr Step BA: Production of Purified Oxidation Feed in Water (OF-c to OF-e)

Oxidation feeds OF-c, OF-d and OF-e were generated by first further purifying additional HMF obtained in the same manner of OF-a (in the absence of a bromine source), in part through using vacuum distillation with a 30 cc Vigreux column (3-4 theoretical plates). Analysis of the vacuum distilled HMF material by gas chromatography, HPLC and NMR showed a purity of between 95 and 96 percent. AcMF was synthesized from a portion of this HMF by reaction with acetic anhydride in acetic acid. NMR analysis confirmed quantitative conversion to AcMF. Excess acetic acid was evaporated off, and the vacuum distilled HMF and AcMF were further purified by crystallization with diethyl ether before being combined with optionally HBr or sugars shown in Table 2) and with glacial acetic acid and optionally water to generate comparative oxidation feeds OF-c, OF-d and OF-e from the further purified furanic materials that were initially generated in the manner of OF-a.

Comparative oxidation feeds with "Purified furanics" (OF-c to OF-e) were generated by taking pure HMF, AcMF, and optionally HBr or sugars and mixing them with glacial acetic acid and optionally water.

The oxidation feed shown in Table 2, entry OF-d provides a comparison to the concentrations of FDCA-forming tiffanies and Br typical for the crude, concentrated integrated process feeds in entries OF-1-4 of Table 2. In the case where Br was added as HBr, the quantity of Br was quantified using the amount of the material added to the purified feed, which was initially free of Br.

Comparative oxidation feed (OF-e) describes a feed also containing 5.0 wt % sugar with a relative distribution of 2:1 of fructose:glucose, providing a sugar composition of 3.3 wt % fructose and 1.7 wt % glucose in solution. Water (20 wt % of total solution) was also added to the oxidation feed solution for OF-e to solubilize the sugars.

Step BB: Oxidation of Purified AcMF and HMF in Acetic Acid

A procedure similar to that described in step 1B was used except that the oxidation feeds of Step BA were used—with purified AcMF and HMF as a source of FDCA-forming furanics in an equivalent concentration to the feeds used in Examples 1-4 (see Table 2, OF-c through OF-e).

Example B.1 demonstrates that inclusion of HBr in an oxidation feed (OF-d) with equivalent concentrations of HMF and AcMF to Example 1 does not alone replicate the high FDCA yields that are shown in Example 1.3 using the integrated process with crude oxidation feed without purification except filtration, even with comparable initial and final Br loadings.

Comparative Examples B.2 and B.3 demonstrate initial catalyst conditions equivalent to those present in Example 3.2. Again, substantially diminished FDCA yields are observed in Comparative Examples B.2 and B.3 compared to Example 3.2. When comparing Comparative Example B.2 to B.3, it can also be shown that presence of sugar in the oxidation feed at concentrations of 5 wt % does not lead to in situ dehydration and oxidation to form FDCA in substantial amounts.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An integrated process for producing 2,5-furandicarboxylic acid and/or a derivative thereof from a six-carbon sugar-containing feed, comprising:
   a) dehydrating a feed comprising a six-carbon sugar unit, in the presence of a bromine source and of a solvent, at an elevated temperature and for a time sufficient to generate an oxidation feed comprised of at least one of 5-hydroxymethylfurfural and/or a derivative or derivatives of 5-hydroxymethylfurfural in the solvent, together with at least one bromine containing species;
   b) removing water from the oxidation feed from step a);
   c) contacting the oxidation feed from step b) with a homogeneous metal catalyst based on Co and Mn and with an oxygen source at an elevated temperature for a time sufficient to produce an oxidation product mixture comprising 2,5-furandicarboxylic acid (FDCA) and/or a derivative thereof, the solvent, and a residual catalyst;
   d) purifying and separating the mixture obtained in step c) to obtain FDCA and/or a derivative thereof and the solvent;
   e) recycling at least a portion of the solvent obtained in step d) to step a); and
   f) providing more or less of the at least one bromine containing species used in step a) in step c), together with optionally other bromine containing species,
   wherein each optionally present derivative is at least one selected from the group consisting of diacid, diether, diester, ether-acid, ether-ester, ester-acid, ester-aldehyde, ether-aldehyde, ether-acetal, ester-acetal, acetal-acid, alcohol-acid, alcohol-ester, alcohol-acetal, diol, diacetal, and aldehyde-acetal.

2. The process according to claim 1, wherein the step of providing more or less of the at least one bromine containing species used in step a) in step c) together with optionally other bromine containing species, comprises adding to or removing bromine containing species from the oxidation feed prior to step c).

3. The process according to claim 1, wherein the bromine containing species in the oxidation feed comprise one or more of an inorganic bromide and organic bromide.

4. The process according to claim 1, wherein the metal catalyst comprises one or more transition metals.

5. The process according to claim 1, wherein the metal catalyst comprises cobalt (II) acetate tetrahydrate, and manganese (II) acetate tetrahydrate.

6. The process according to claim 1, wherein the metal catalyst further comprises Zr.

7. The process according to claim 1, wherein the metal catalyst further comprises Ce.

8. The process according to claim 1, wherein the bromine source in step a) comprises hydrogen bromide.

9. The process according to claim 1, wherein the feed to the dehydration step comprises one or more of starch, amylose, galactose, cellulose, hemicellulose, inulin, fructan, glucose, fructose, sucrose, maltose, cellobiose, lactose, and sugar oligomers.

10. The process according to claim 1, wherein the solvent comprises acetic acid or a mixture of acetic acid and water.

11. The process according to claim 1, wherein the feed is dehydrated in the further presence of a $C_1$-$C_5$ alcohol.

12. The process according to claim 1, wherein the oxidation step is performed at a temperature of from about 120 to about 250 degrees Celsius and at an oxygen partial pressure of from about 0.02 to about 100 bar.

13. The process according to claim 1, further comprising esterifying 2,5-furandicarboxylic acid with a $C_1$-$C_{12}$ aliphatic alcohol or a $C_1$-$C_{12}$ aliphatic diol, under conditions effective for carrying out the esterification and optionally in the presence of a suitable esterification catalyst.

14. The process according to claim 1, further comprising preparing a polyester by transesterification of at least one ester of 2,5-furandicarboxylic acid with a $C_2$ to $C_{12}$ aliphatic diol or a polyol and optionally at least one of a polyalkylene ether glycol (PAEG), a polyfunctional acid or a polyfunctional hydroxyl acid.

15. The process according to claim 2, wherein the bromine containing species in the oxidation feed comprise one or more of an inorganic bromide and organic bromide.

* * * * *